US00RE37803E

(19) United States
(12) Reissued Patent
Kusaba et al.

(10) Patent Number: US RE37,803 E
(45) Date of Reissued Patent: Jul. 23, 2002

(54) CHEMICAL DATA HANDLING SYSTEM

(75) Inventors: Shigeki Kusaba, Minoo; Futoshi Imamura, Takatsuki; Masako Yamamoto, Osaka; Kaoru Mori, Settsu, all of (JP)

(73) Assignee: Fujitsu Limited, Kanagawa (JP)

(21) Appl. No.: 08/616,225

(22) Filed: Mar. 15, 1996

Related U.S. Patent Documents

Reissue of:
(64) Patent No.: 5,321,804
Issued: Jun. 14, 1994
Appl. No.: 07/725,103
Filed: Jul. 3, 1991

(30) Foreign Application Priority Data

| | | |
|---|---|---|
| Jul. 5, 1990 | (JP) | 2-179781 |
| Jul. 5, 1990 | (JP) | 2-179782 |
| Jul. 5, 1990 | (JP) | 2-179783 |
| Aug. 10, 1990 | (JP) | 2-212809 |
| Sep. 17, 1990 | (JP) | 2-248032 |

(51) Int. Cl.[7] ..... G06F 15/00
(52) U.S. Cl. ..... 395/334
(58) Field of Search ..... 395/142, 143, 395/333, 334, 335; 345/440, 441, 442

(56) References Cited

U.S. PATENT DOCUMENTS 5,168,554 A * 12/1992 Luke ..... 395/161
5,187,775 A * 2/1993 Schroeder et al. ..... 395/155

FOREIGN PATENT DOCUMENTS

| | | |
|---|---|---|
| JP | 62-189562 | 8/1987 |
| JP | 63-118876 | 5/1988 |
| JP | 63-165963 | 7/1988 |
| JP | 1-114984 | 5/1989 |
| JP | 2-28879 | 1/1990 |
| JP | 2-81270 | 3/1990 |

OTHER PUBLICATIONS

"Hajimete Tsukau LOTUS 1–2–3", Shiobara, *Gijutsu Hyoron Sya,* 1987, pp. 47–48.
"Computer Graphics in Chemical CAD", Koide, *Joho Syori,* vol. 29, No. 10, 1988, pp. 1182–1189.

* cited by examiner

*Primary Examiner*—Phu K. Nguyen
(74) *Attorney, Agent, or Firm*—Arent Fox Kintner Plotkin & Kahn PLLC

(57) ABSTRACT

A chemical data handling system is characterized by a display system which displays each data of many compound with an image of a table sheet where the chemical structures are arranged in the direction X and general characteristic data items are arranged in the direction Y. For realizing the display of the entire large scale data table, the system provides a special scroll function. In the case of lateral scroll, the chemical structure display column arranged vertically is fixed at the left side of screen, and the remaining data columns are scrolled laterally. In the case of a vertical scroll, the data item display row arranged laterally is fixed at the upper side of screen, and the remaining data rows are scrolled vertically. Moreover, it is possible to display not only the data table but also a chemical structure list or a chemical data correlation graph.

21 Claims, 19 Drawing Sheets

CHEMICAL DATA HANDLING SYSTEM

Matter enclosed in heavy brackets [ ] appears in the original patent but forms no part of this reissue specification; matter printed in italics indicates the additions made by reissue.

BACKGROUND OF THE INVENTION

Field of the Invention

The present invention relates to a chemical data handling system and particularly to a new chemical data handling system for storing and orderly arranging the structures of compounds or material data within a memory and for displaying such data in the form suitable for application.

In the chemical and pharmaceutical industries, investigators deal with many kinds of compounds, and enormous time and labor are required for the orderly arranging of chemical structure data for such compound and general data If such chemical data can be arranged easily and orderly arranged chemical data can be reedited, the investigators can thus spend more of their time for investigations.

Therefore, advent of data handling system for easily arranging or editing chemical data and also easily displaying the orderly arranged chemical data for investigators has long been expected.

Description of the Prior Art

Many investigators in the chemical and pharmaceutical industries prepare for a large amount of compounds and conduct testing of these compounds for the development of a new and useful chemical materials. Since the structure and characteristics of a certain compound can give a hint for trying other samples, the arrangement of test data is very important for investigators. However, an adequate tool for supporting the arrangement of data by investigators has not yet been proposed. Therefore, almost every investigator has recorded data, although it may be a extremely primitive method, by utilizing a notebook or a large size table sheet. However, writing a data table of compounds into a large size paper is inferior from the point of view of effective use of space within the investigation room because a wider area is required to enter necessary items and to post the written table.

Moreover, when data is written in a plurality of pages, all the data cannot be observed at one time. Accordingly, when a chemical structure and characteristics of a certain compound are described an different pages, for example, searching through the different pages is required for considering the relationship between the chemical structure and the compound's characteristics. Moreover, when a page is turned over, an investigator is inevitably required to take his eyes off from one notable area to another, and therefore the flow of the thinking of investigator can be interrupted.

In any case, many hours and much labor are required for editing the compound data table once generated, and such editing is very difficult.

SUMMARY OF THE INVENTION

It is therefore a principal object of the present invention to provide a new tool for handling and displaying chemical data in order to support the investigation by investigators in the field of chemistry.

It is another object of the present invention to provide a chemical data handling system which is capable of displaying chemical data including chemical structural formulas in the image of a data sheet on a display.

It is a further object of the present invention to provide a chemical data display system which is capable of displaying a large amount of data including chemical structural formulas in a selectable multimode in order to support the thinking and analysis from various aspects by investigators in the field of chemistry.

It is an even further object of the present invention to provide a chemical data handling system having an editing function to enable accurate copying of data between data tables generated in the sheet image.

It is a further object of the present invention to provide a chemical data handling system having a special expression for the display of chemical structural formulas on the display.

In summary, in order to attain such objects, the present invention stores chemical structural data and general data corresponding to each chemical structure within a memory file based on that correspondence. The chemical data handling system of the present invention is characterized by a display system which displays each data with an image of a table sheet where the chemical structures are arranged in the direction X (or direction Y) and general data items in the direction Y (or direction X). The data table to be displayed on the display has a large scale for allowing the entry of data on many compounds. Accordingly, the total display can be realized by scroll operation. In this case, as the first characteristic of the present invention, the chemical structure display column arranged vertically (direction X) are fixed at the left side of screen, in the case of the lateral (Y) scroll and the remaining data column is scrolled lateral. On the other hand, the case of the vertically (X) scroll, the data item display rows arranged laterally (direction Y) are fixed at the upper side of screen and the remaining data rows are scrolled vertically. In any case, chemical structures are displayed as the key columns.

As a second characteristic of the chemical data handling system of the present invention, a function for displaying a list of all chemical structures entered in the table is also added. The other features and utilities of the present invention will be made obvious from explanation about the embodiment thereof.

DESCRIPTION OF THE PREFERRED EMBODIMENTS

1st Embodiment

Figure 1:
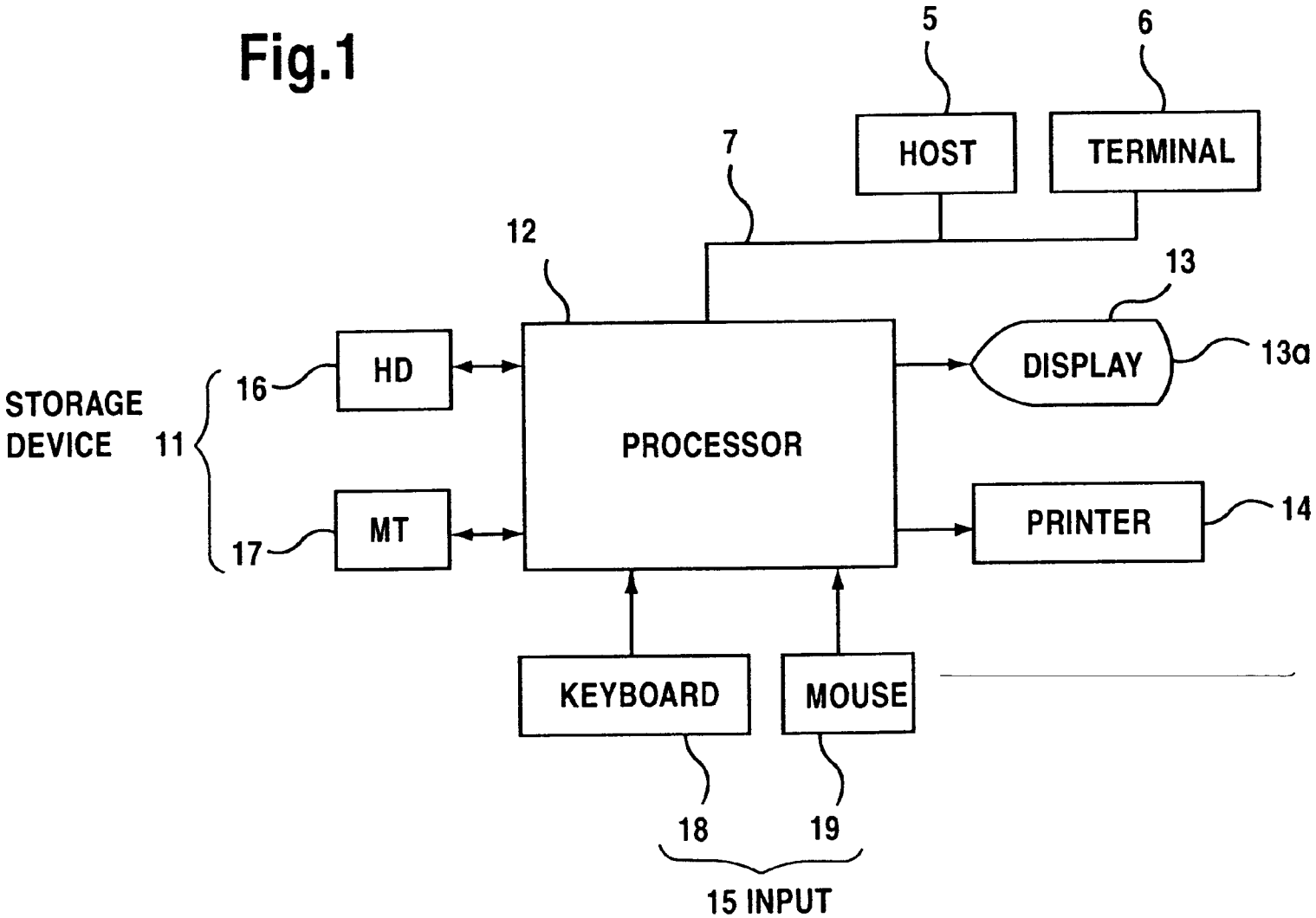
FIG. 1 is a block diagram indicating the entire construction of a chemical data handling system of the present invention.

FIG. 1 is a block diagram indicating a construction of a chemical data handling system according to the present invention.

This system comprises a storage device 11 consisting of a hard disk 16 or magnetic tape reader 17, a processing unit 12 utilizing a microprocessor, a display unit 13 comprising a screen 13a, a printer 14, and an input unit 15 such as keyboard 18 or mouse 19. This structure can be realized, for example, using a work station or a personal computer. This system is used as an individual unit and moreover is capable of realizing incorporated operation through connection with a host computer 5 and other terminal units 6 via the communication line 7.

The storage device 11 stores programs required for processings or controls in the system as a whole and various chemical data such as compound data DC and data item name DH, etc. On the screen 13a of display unit 13, data table TD (described later), other data and images are displayed. Printing of data table TD or data sheet SD, or producing a hard copy of screen 13a are carried out by the printer 14. From an input unit 15, a command for displaying data table TD to the screen 13a, a command for scrolling data table TD, a command required for processing in the other processing unit 12 as well as data can be inputted.

Next, the display operation of data table TD by the system described above will be explained with reference to FIG. 2.

Figure 2:
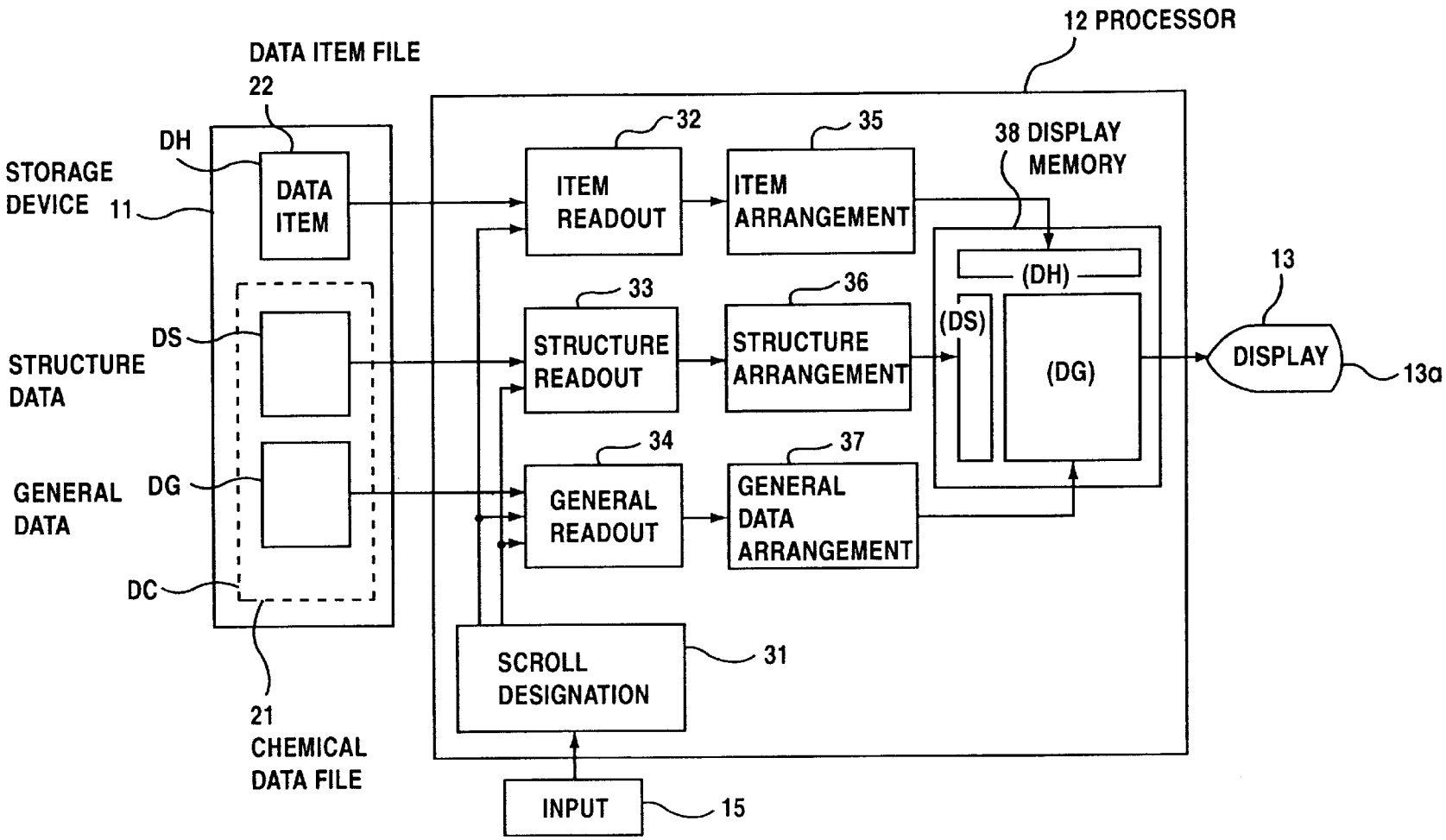
FIG. 2 is a block diagram indicating a functional construction of a chemical data display system in a first embodiment.

FIG. 2 is a block diagram functionally indicating a system construction of the present invention.

Within the storage device 11, a plurality of compound data files 21 storing, for each compound, compound data DC consisting of chemical structure data DS for compounds and general data DG, and a data item name file 22 storing data item names DH corresponding to compound data DC are generated.

The chemical structure data DS indicates mutual coupling of atoms forming a compound and is displayed on the screen 13a as plane structural formulas or cubic structural formulas.

The general data DG indicates the nature of the compounds indicated by chemical structure data DS.

The data item of general data DG differs depending on the kinds of compounds involved. For example, if a compound is a drug, the general data DG includes data items of Generic name, Drug code number, Brand name, Manufacturer, Therapeutic category, Mechanism, Administration, Salt, Fragment, Electronic density, Total energy and Volume. Selection of the data item and the name for displaying the data item (data item name DH) can be changed depending on the purpose for generating a data table TD, on the application field of the compound and on the application purpose.

The data item name DH becomes a head line of each data of general data DG and chemical structure data DS, and it is practically indicated as an above example. The data item name DH of the chemical structure data DS is displayed, for example, as "Structure".

The compound data file 21 and data item name file 22 are generated by inputting the necessary data in the data input mode, or down-loading from a host computer 5 or terminal unit 6. They are also supplied by setting a magnetic tape storing generated files into a storage device 11.

Figure 3:
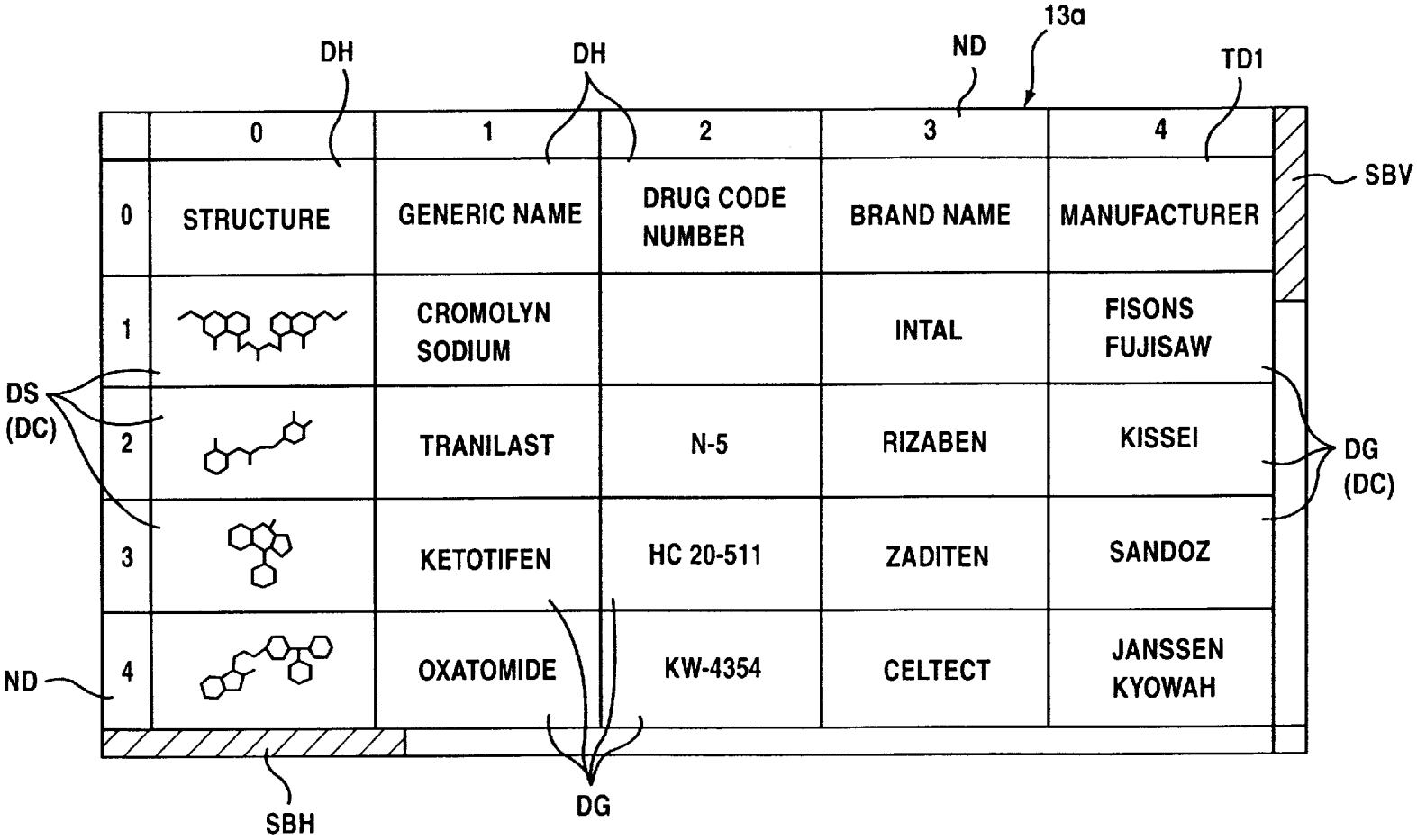
FIG. 3 is a diagram indicating an example of displayed data table.

The processor 12 reads, with a command from the input unit 15, compound data DC and data item name DH from the storage device 11 and writes the data to the display meory 38 in the predetermined arrangement and then displays the data, as shown in FIG. 3, as the data table DT on the screen 13a of the display unit 13. For the entry to display memory 38, a bit map format or data list format is introduced.

In general, investigators deal with a large amount of compound data DC and data item names DH. Therefore, the data table can become large in the scale. It is accordingly difficult to simultaneously display all the data in the screen 13a. Therefore, the data table TD to be written into the display memory 38; the data table to be displayed on the screen 13a is displayed by scrolling only the data at the position indicated on the basis of the scroll command sent from the input unit 15.

Namely, all data item names DH and compound data DC stored in the data item name file 22 and a series of compound data files 21 corresponding thereto form the one data base DB and also form the one imaginary data sheet SD. The data table TD of FIG. 3 is a part of the data sheet DS displayed on the screen 13a and the entirety of data sheet SD can be displayed by scrolling. The storage device 11 is capable of storing a plurality of data bases, and data transfer and copying can be realized between these data bases DB.

In the embodiment shown in FIG. 2, the processor 12 comprises a scroll instruction means 31 for instructing horizontal and vertical scrolls of screen 13a with a command from the input unit 15; a data item name readout means 32 for reading, from the data item name file 22, data item name DH corresponding to chemical structure data DS and data item name DH at the position in the horizontal direction instructed by the scroll instruction means 31; a chemical structure data readout means 33 for reading chemical structure data DS at the position in the vertical direction instructed by the scroll instruction means 31 and an general data readout means 34 for reading general data DG at the position instructed by the scroll instruction means 31. The data item name DH read by the data item name readout means 32 is written into the displaya memory 38 and arranged in the horizontal directioin on the screen 13a by the data item arranging means 35. The chemical structure data DS read from the chemical structure data file DS is written into the display memory 38 so that this data is arranged in the vertical direction on the screen 13a at the column corresponding to the data item name DH of "Structure" by the chemical structure data arranging means 36. Moreover, general data DG read from the general data file DG is written into the display memory 38 so that it is arranged at the ordinary data arranging means 37 at the crosspoint on the screen 13a corresponding to the data item name DH and chemical structure data DS. In actuality, these means are realized by execution of processing programs in the processing unit 12.

Figure 4:
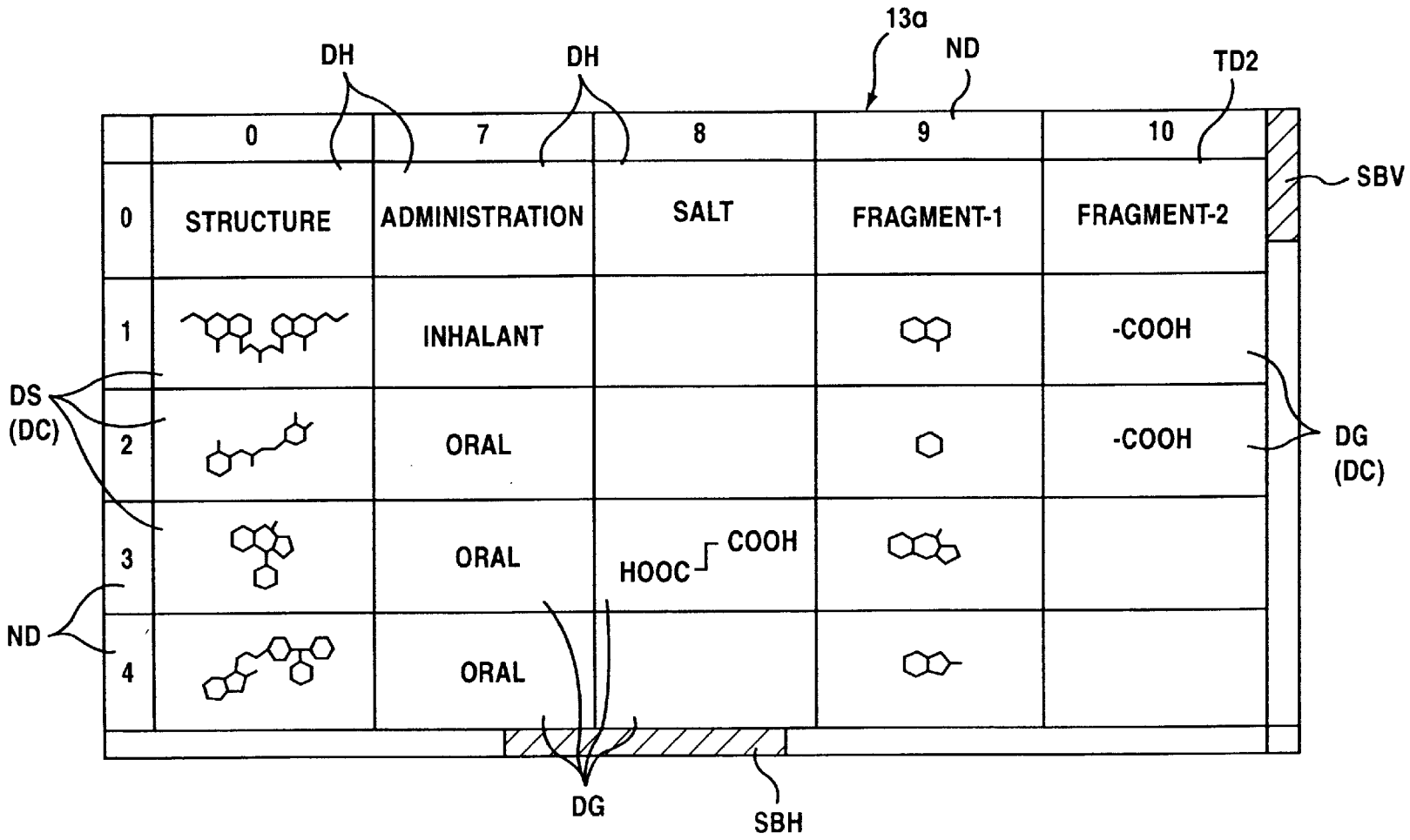
FIG. 4 is a diagram indicating the horizontally scrolled condition of the data table of FIG. 3.
Figure 5:
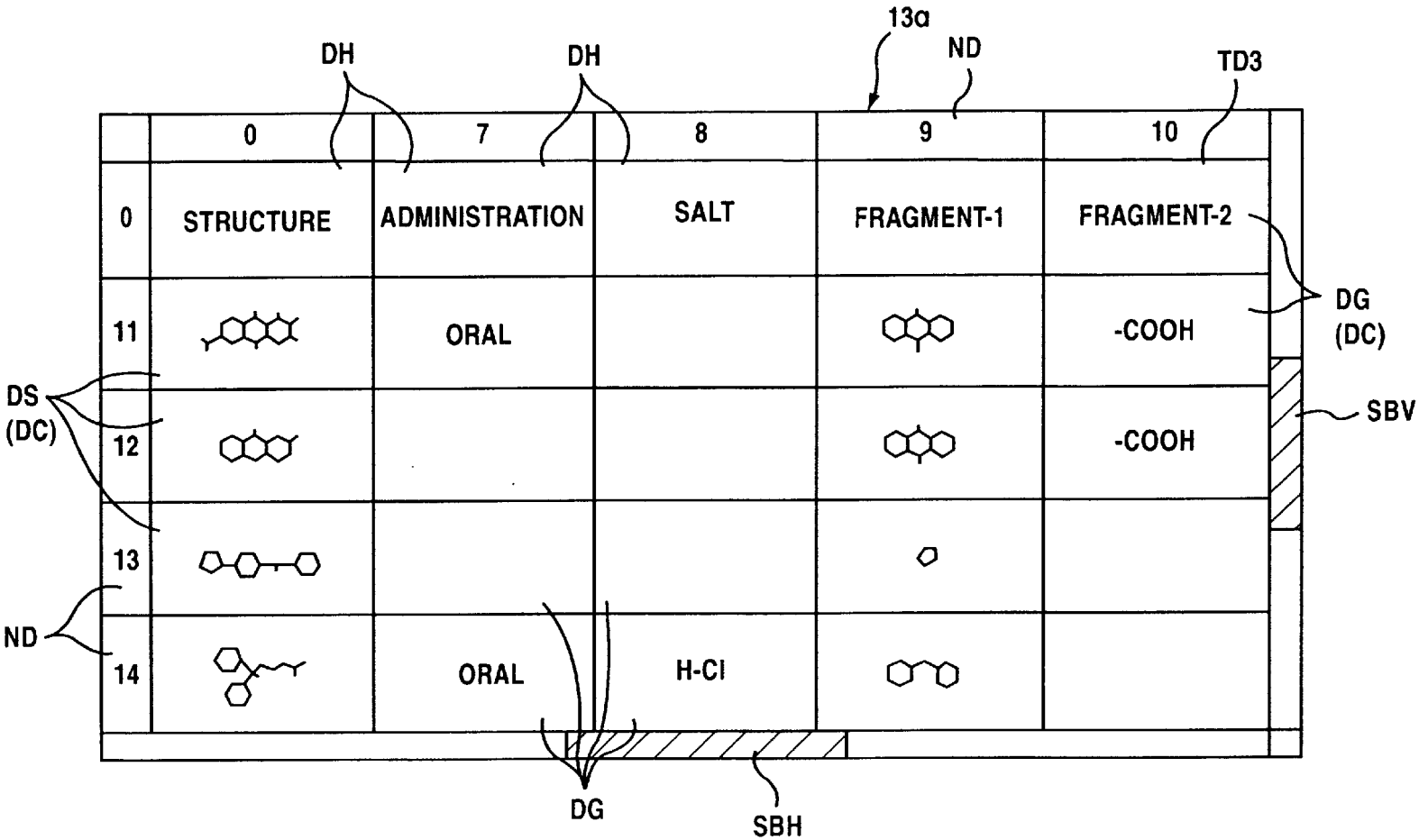
FIG. 5 is a diagram indicating the vertically scrolled condition of the data table of FIG. 4.

With reference to FIGS. 3 to 5 indicating display samples of data tables, the data number ND of data to be displayed is respectively displayed in the horizontal direction at the upper end portion and the vertical direction at the left end portion on the screen 13a. The scroll bars SBH, SBV indicating the scroll positions in the horizontal and vertical directions are displayed in the horizontal direction of lower end portion, respectively and right end portion. The data table TD is displayed at the inside thereof. In the data table TD, the data item name DH is arranged and displayed in the horizontal direction (row) at the upper most stage, while the chemical structure data DS in the vertical direction (column) at the left end and general data DG at the positions corresponding to the intersecting points of rows and columns.

The data table TD1 shown in FIG. 3 is displayed in the initial screen displayed immediately after the instruction for displaying data table TD is issued. In the initial screen, the leading part of data sheet SD is displayed. Accordingly, in the screen shown in FIG. 3, the scroll bars SBH, SBV are respectively located at the left end or upper end portion.

The data table TD1 displays the data item name DH of data numbers ND from 0 to 4, chemical structure data DS of data numbers ND from 0 to 4 and general data DG corresponding to such data.

The data table TD2 shown in FIG. 4 is displayed by scrolling the data table TD1 in the horizontal direction. The data table TD2 displays the chemical structure data DS which is the same as that of the data table TD1, and also displays the general data other than "Structure" which is scrolled in the horizontal direction and corresponds to the data item name DH having the data numbers ND from 7 to 10.

In particular, when the scroll in the horizontal direction is instructed by a mouse 19 of input unit 15 through the scroll instruction means 31, the column of chemical structure data DS is not scrolled but only the columns of general data are scrolled horizontally.

On the other hand, the data table TD3 shown in FIG. 5 is a display screen when the data tabale TD2 is scrolled in the vertical direction. In the data table TD3, rows of the chemical structure data DS and general data DG corresponding thereto are vertically scrolled and thereby the chemical structure data DS of the data numbers from 11 to 14 in place of that from 1 to 4 and the general data DG of the data numbers from 7 to 10 are displayed.

Specifically, when the vertical scroll is instructed, the data item name DH is not scrolled and rows of only the chemical structure data DS and general data DG are scrolled.

Figure 6:
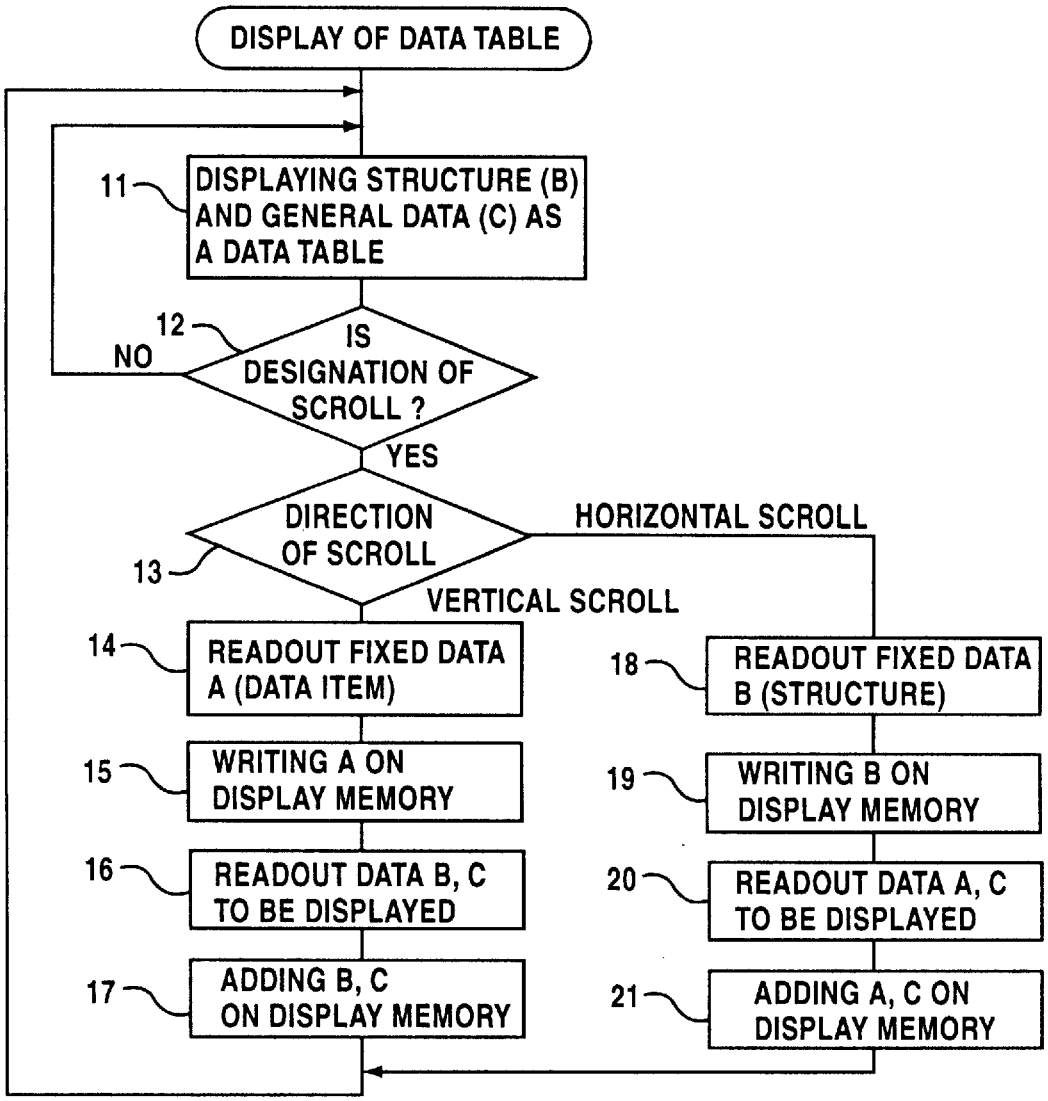
FIG. 6 is a flowchart indicating an outline of the display operation of a chemical data table.

FIG. 6 shows a flowchart of the display operation. First, as the initial table screen, the upper left portion of the data table is displayed (step #11) like the data table TD1 of FIG. 3. Next, when a scroll instruction is inputted (step #12), the direction is determined (step #12) and the operation skips to the next step. An instruction for scroll operation can be given from a mouse 19 as an input means, while observing the display of the scroll bars SBH, SBV.

When the vertical scrolling is instructed, the data item name DH is read out (step #14) as the fixed display information and this data is put in the display memory 38 (step #15). Next, the chemical structure data DS and general data DG of the display object area are read out (step #16) in accordance with the width of the scroll and such data is written (step #17) to the predetermined area of display memory 38. Thereafter, contents of display memory are displayed (step #11). On the other hand, in case the horizontal scroll is instructed, the chemical structure data DS is read out as the fixed information (step #18) and then written into the display memory (step #18). Next, the data item name DH and general data DG of the part to be displayed in accordance with the width of the scroll are extracted (step #19) and then added to the display memory (step #20). Thereafter, the horizontally scrolled table can be displayed (step #11) by displaying contents of the display memory.

According to the embodiment explained above, an imaginary data sheet SD formed by many chemical structure data DS, general data DG and data item names DH can be displayed as the data table TD on the screen 13a and the entirety of data sheet SD can be displayed in accordance with the scroll instruction from the input unit 15.

Moreover, in the case of a horizontal scroll, the chemical structure data DS is not scrolled and it is always displayed on the screen 13a. Therefore, correspondence between the general data DG and the compound can always be detected, and the chemical structure data DS can be considered as the key for analyzing by an operator (investigator). Moreover, since the data item name DH is not scrolled and it is always displayed on the screen 13a at the time of vertical scrolling, it is very convenient for understanding the contents of general data DG.

Accordingly, when the data table TD is scrolled, the investigator is no longer required to take his eyes off from a notable area in order to turn pages as in the conventional case, and he is never placed out of the flow of continuous thinking and analysis.

Moreover, the data sheet SD formed by compound data DC and data item names DH is all imaginary data. Therefore, even through such a data sheet is very large, it does not require space for posting it thereby allowing space in the investigation room to be used more effectively.

2nd Embodiment

Next, a second embodiment of the present invention will be explained. The second embodiment is characterized by adding the function for displaying a chemical structure table to the data table display function utilizing a chemical structure fixing scroll just as explained in the first emboidment.

Figure 7:
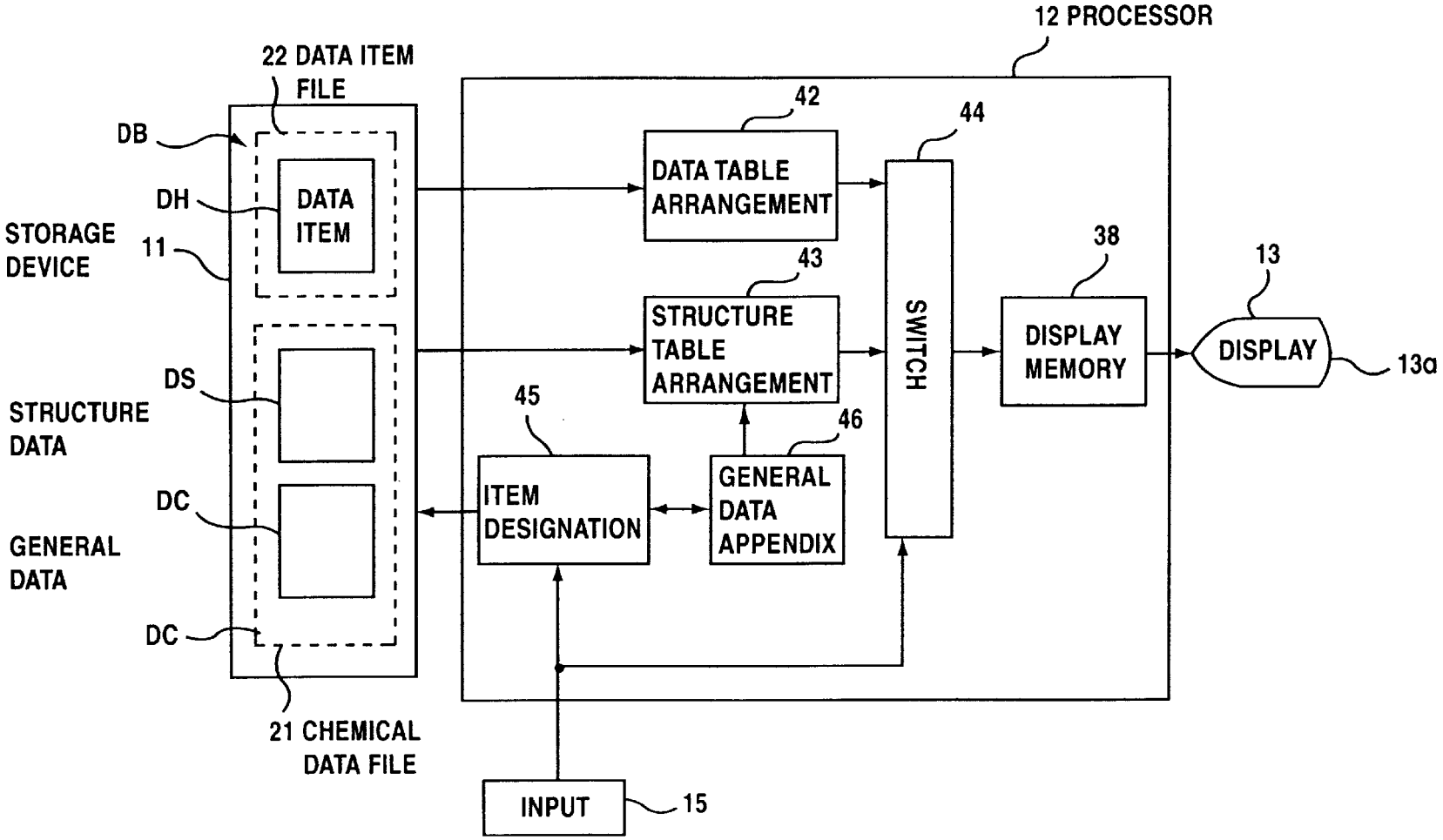
FIG. 7 is a block diagram indicating a functional construction of a chemical data display system in a second embodiment.

With reference to FIG. 7 indicating a system construction with a functional block diagram, the same reference numeral is labeled to the element equivalent to that of FIG. 2. In the processing unit 12, the compound data table arranging means 42 represents the means (31 37) for reading and arranging the data to be displayed as the data table which has been explained previously with reference to FIG. 2. As the new elements, a structure table arranging means 43, a switching means 44, a data item name designating means 45 and a general data labeling and arranging means 46 are added.

Therefore, according to this system, in the case where the data base DB stored in the storage device 11 is entirely or partly displayed with a command from the input unit 15, a table display mode or structure table display mode is designated as the display mode and these display modes can be switched for display on the screen 13a.

Namely, in the table display mode, the compound data table arranging means 42 in the processing unit 12 writes the chemical structure data DS (structure formula) of each compound to the display memory 38 arranging it in the vertical direction on the screen 13a, and general data DG of chemical structure data DS and data item name DH arranging it in the horizontal direction and then displays these data as the data table TD of FIG. 3 on the screen 13a.

Figure 8:
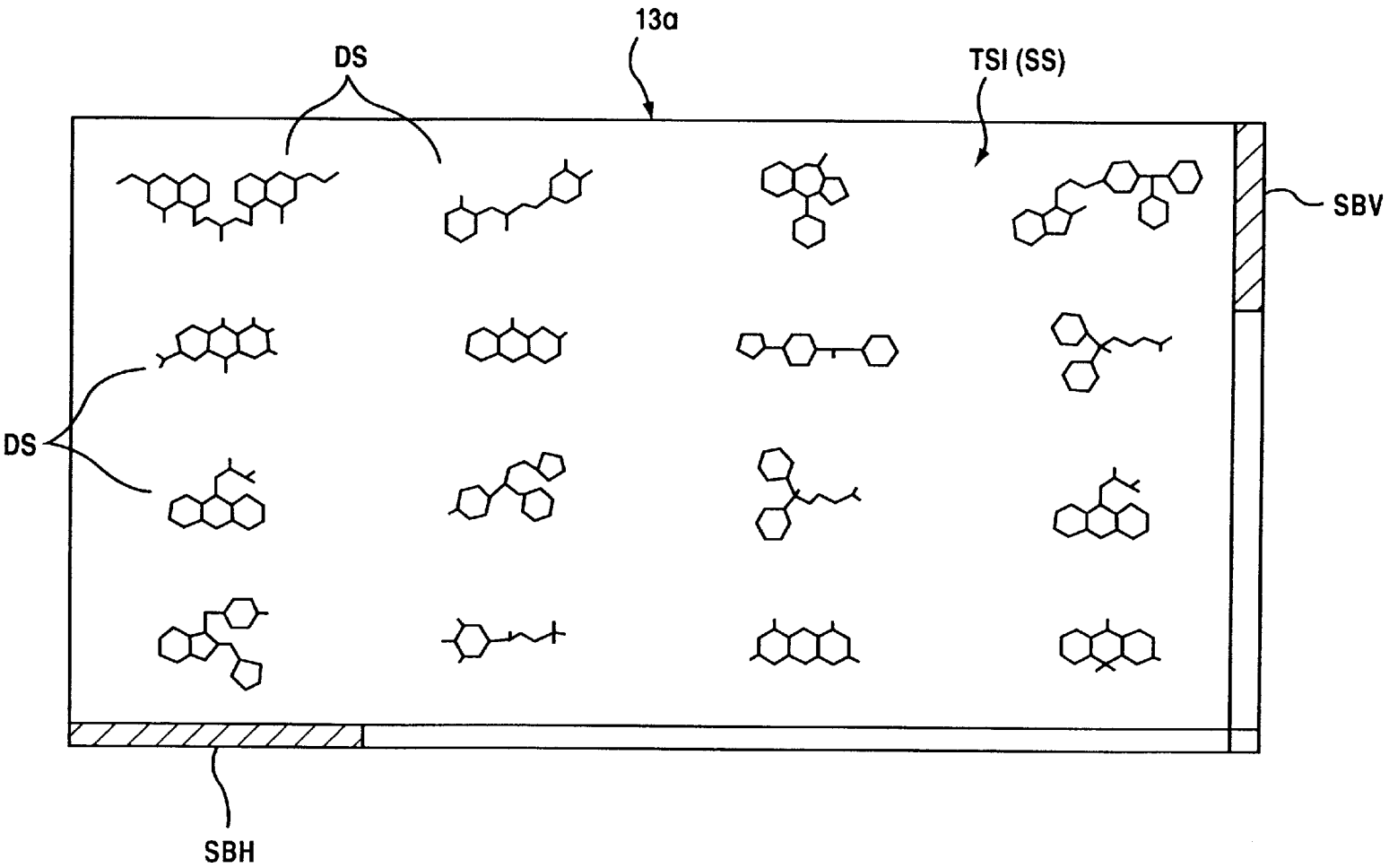
FIG. 8 is a diagram indicating an example of a table displayed by the chemical structure list display mode.

On the other hand, in the structure table display mode, the processing unit 12 arranges horizontally and vertically chemical structure data DS of each compound in the form of a matrix and displays as a structure table TS as shown in FIG. 8 on the screen 13a.

In this case, the general data DG of designated data item names DH can be displayed in such a form as adding it as a parameter in the vicinity of the chemical structure data DS by designating the one or a plurality of data item names DH from the input unit 15 through the item name designating means 45. The screen TS2 of such a display mode is shown in FIG. 9.

Even in the structure table display mode, if there is a large quantity of chemical structure data DS and general data DG and it is impossible to simultaneously display such data on the screen 13a, only the data at the position instructed on the basis of the scroll instruction from the input unit 15 is scrolled and displayed as explained above. Namely, a sheet of large imaginary structure table sheet SS is formed by all chemical structure data DS included in the one database DB and a part of such a structure table is displayed on the screen 13a as the structure table TS. The entirety of the structure table sheet SS can be dislayed by scrolling.

According to the structure table TS1 shown in FIG. 8, many chemical structures are adjacently displayed like a matrix and therefore many chemical structures can be compared simultaneously as a whole. Thereby, it is possible to conduct discussions and analyses from the entire viewpoint on the basis of the experience and knowledge of investigator, just like investigating the causes and results of the chemical structure of a certain compound having a particular nature. Moreover, since the table display mode and structure table display mode can be quickly switched by the input unit 15, the investigator's analysis and train of thought need not be interrupted.

Figure 9:
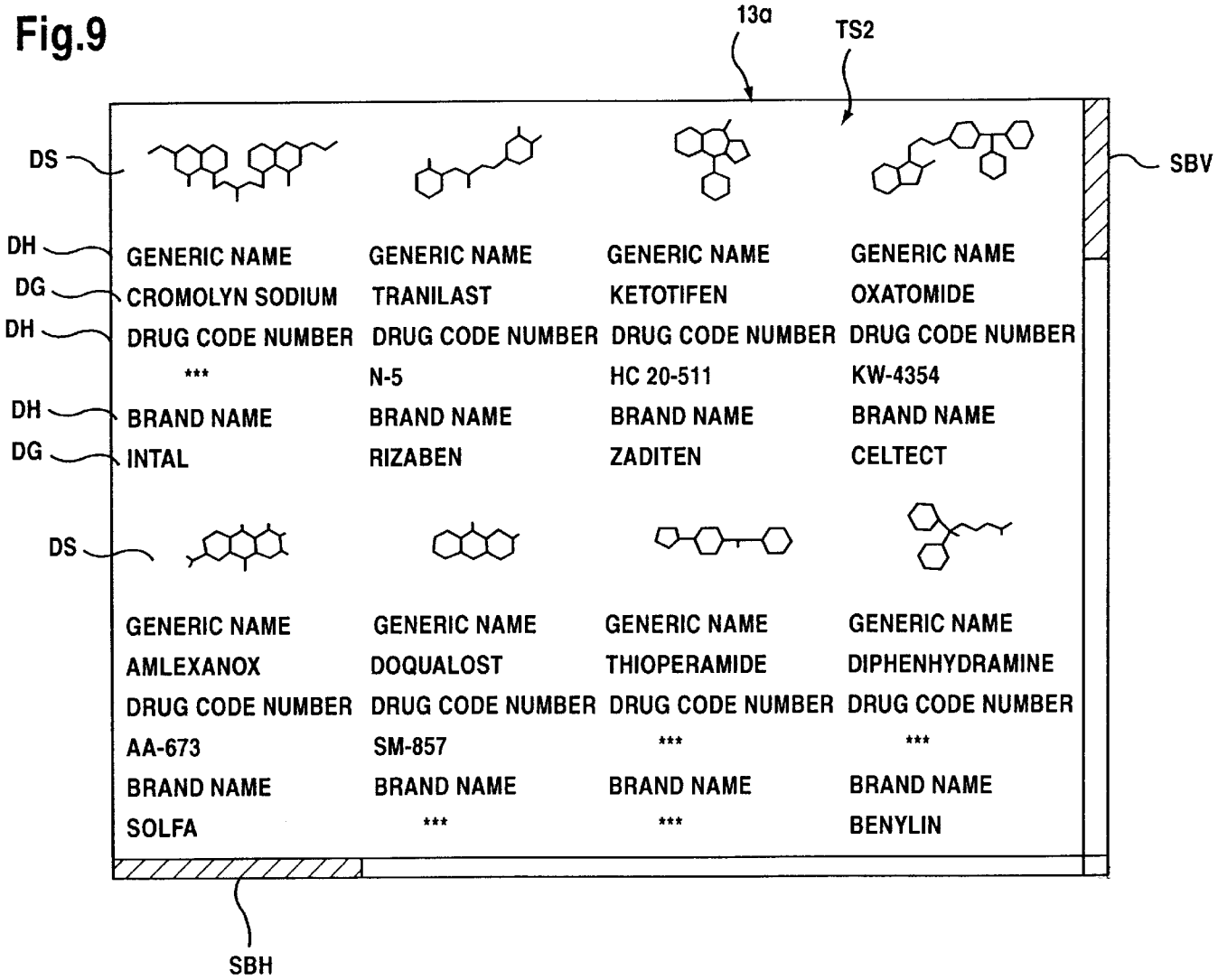
FIG. 9 is a diagram for indicating another display example of the chemical structure list display.

According to the structure table TS2 shown in FIG. 9, the general data DG required by investigators are displayed together with chemical structures and these can be compared and discussed generally. For designation of a data item name DH to be added to the chemical structure, a list of data item names DH is displayed in the subwindow by the input unit 15 and necessary data item names are selected and designated from this list. During the subwindow display, the designated data item name DH is emphasizingly displayed. Designation, addition or alteration of data item name DH can be realized as required in the structure table display mode.

Figure 10:
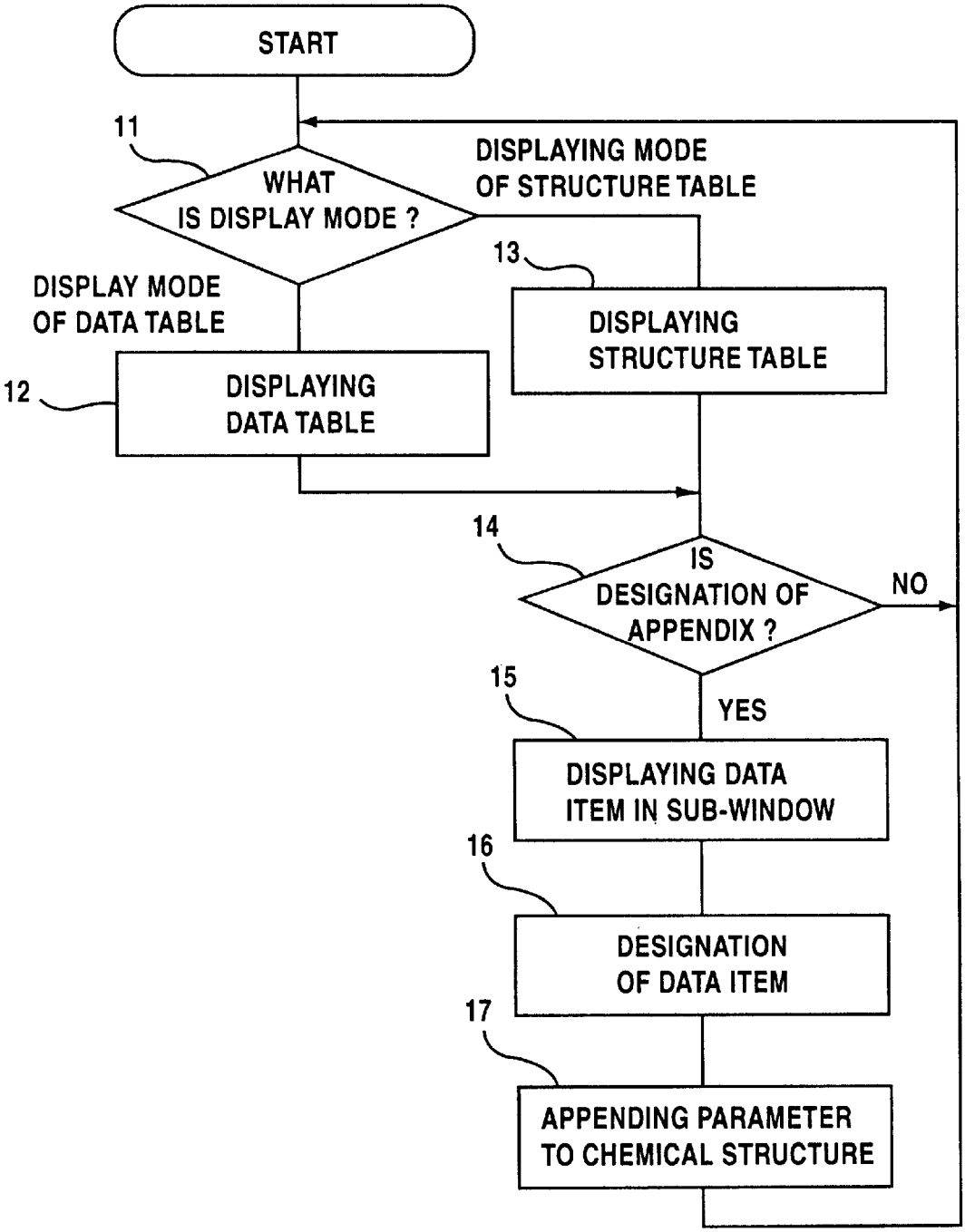
FIG. 10 is a flowchart indicating an outline of the display mode switching operation in a second embodiment.

FIG. 10 is a flowchart indicating the outline of display processing by the display unit 1.

First, in case the display mode is set to the table display mode (step #11), the data table TD is displayed on the screen 13a (step #12).

When the display mode is set to the structure table display mode, the structure table TS is displayed on the screen 13a (step #13).

When an additional display is instructed (step #14), data item names DH are displayed in the subwindow on the screen 13a (step #15), a desired data item name DH is designated (step #16), the general data DG of the designated data item name is arranged so that it is additionally displayed as the parameter in the vicinity of the chemical structure (step #17), and these are displayed on the screen 13a as the structure table TS (step #13).

3rd Embodiment

The third embodiment of the present invention is characterized by a chemical data handling system providing a function to display the correlation of physical materials of a plurality of compounds as graphs.

Namely, in the correlation diagram display mode, a couple of designated physical material names (data item names DH) are plotted on the XY plane with each compound plotted based on the physical material data DM and the most approximated straight line AL for the plotting points PP that can be obtained arithmetically and displayed.

When the plotting points PP on the screen 13a are designated, the chemical structure CC of the compound corresponding to the designated plotting points PP is displayed at the lower right position of relevant plotting points PP.

Figure 11:
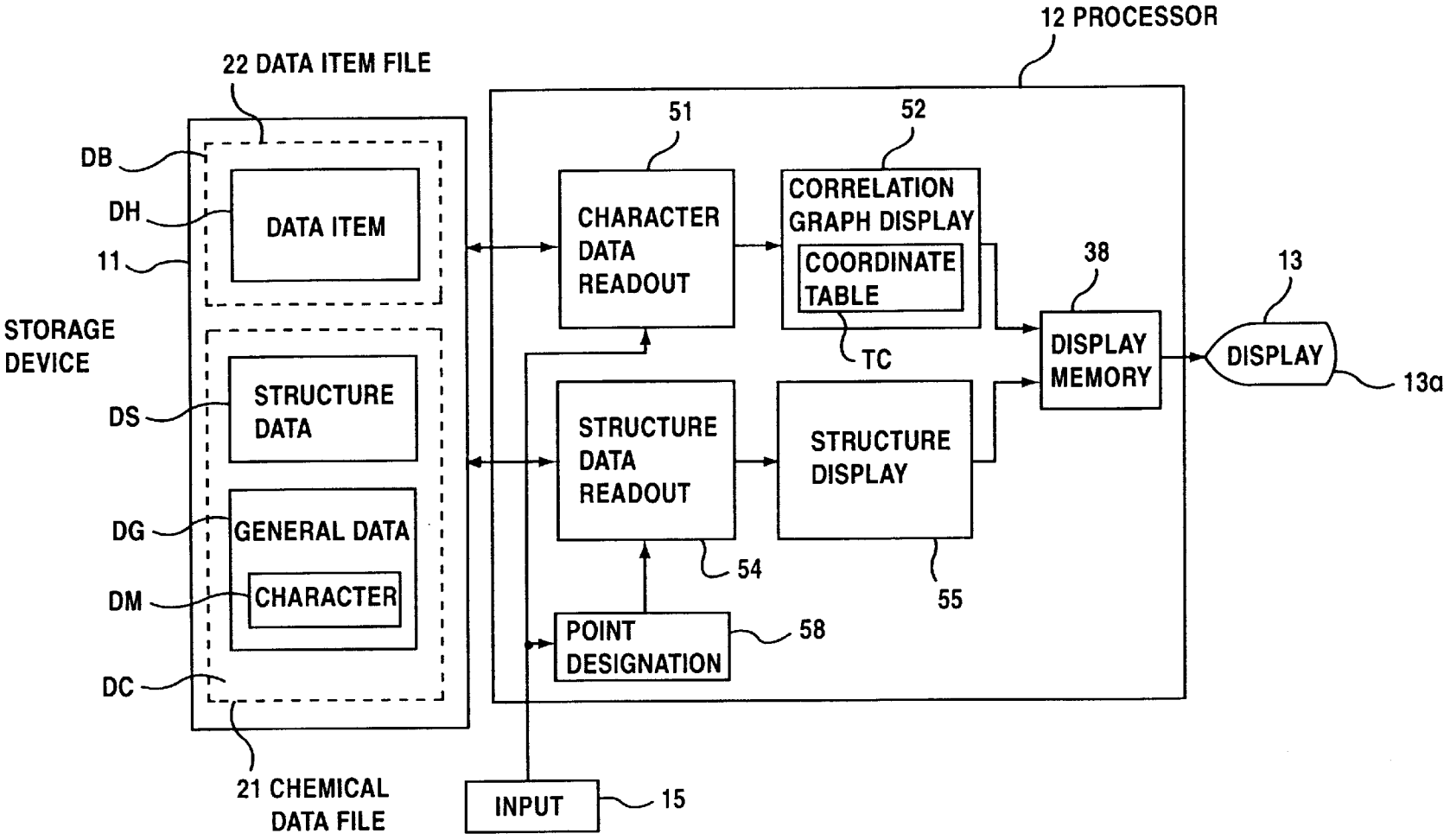
FIG. 11 is a block diagram indicating a functional construction of a chemical data display system in a third embodiment.

In order to display the correlation graph CD, an embodiment shown in FIG. 11 comprises a physical material data readout means 51 for reading physical material data DM of the designated material from a database DB, a correlation graph display means 52 for displaying a correlation graph CD based on the physical material data obtained, a plotting point designation means 53 for designating the plotting points PP of the correlation graph CD, a chemical structure data readout means 54 for reading chemical structure data DS at the designated plotting points PP from a database DB, and a chemical structure display means 55 for displaying a chemical structure CC on the screen 13a based on the chemical structure data DS obtained.

Here, in the correlation graph display means 52, a coordinates table TC storing coordaintes data obtained arithmetically from the physical material data DM is generated. Moreover, the chemical structure data readout means 34 and processing unit 12 are respectively provided with work areas for temporarily storing data.

Each means is realized by execution of the processing program in the processing unit 12.

Figure 12:
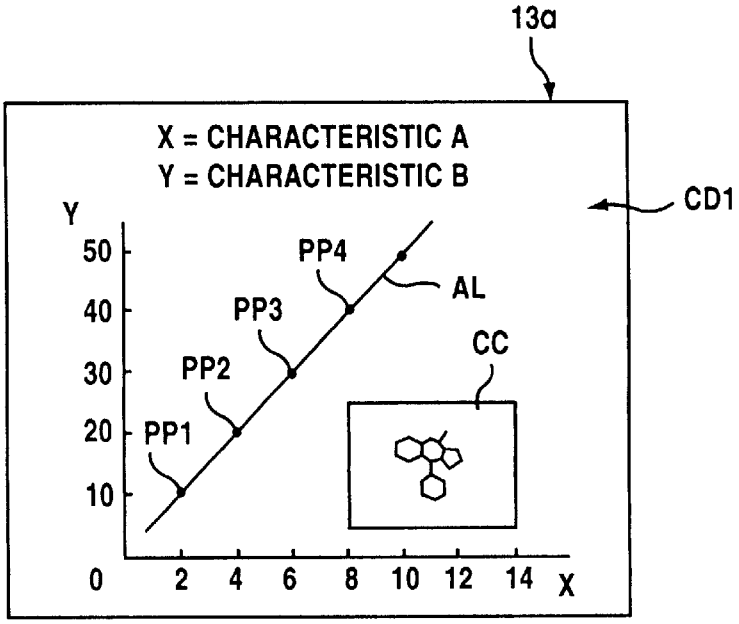
FIG. 12 is a diagram indicating an example of a chemical data correlation graph displayed in a third embodiment.

FIG. 12 shows an example of the physical material data correlation graph CD1 displayed on the screen 13a.

In this correlation graph CD1, a physical material A is designated on the axis X, while a material B on the axis Y. The compounds having compound numbers ND are plotted on the XY plane like the plotting points PP1, PP2, PP3 . . . based on the respectively physical material data DM. Moreover, the most approximated straight line AL for the plotting points PP is displayed in the correlation graph CD1. In addition, a chemical structure CC for the plotting point PP3 designated by the mouse of input unit 15 is displayed in the window on the screen 13a.

Next, the processing sequence for displaying the correlation graph CD1 will be explained on the basis of the flowchart.

Figure 13:
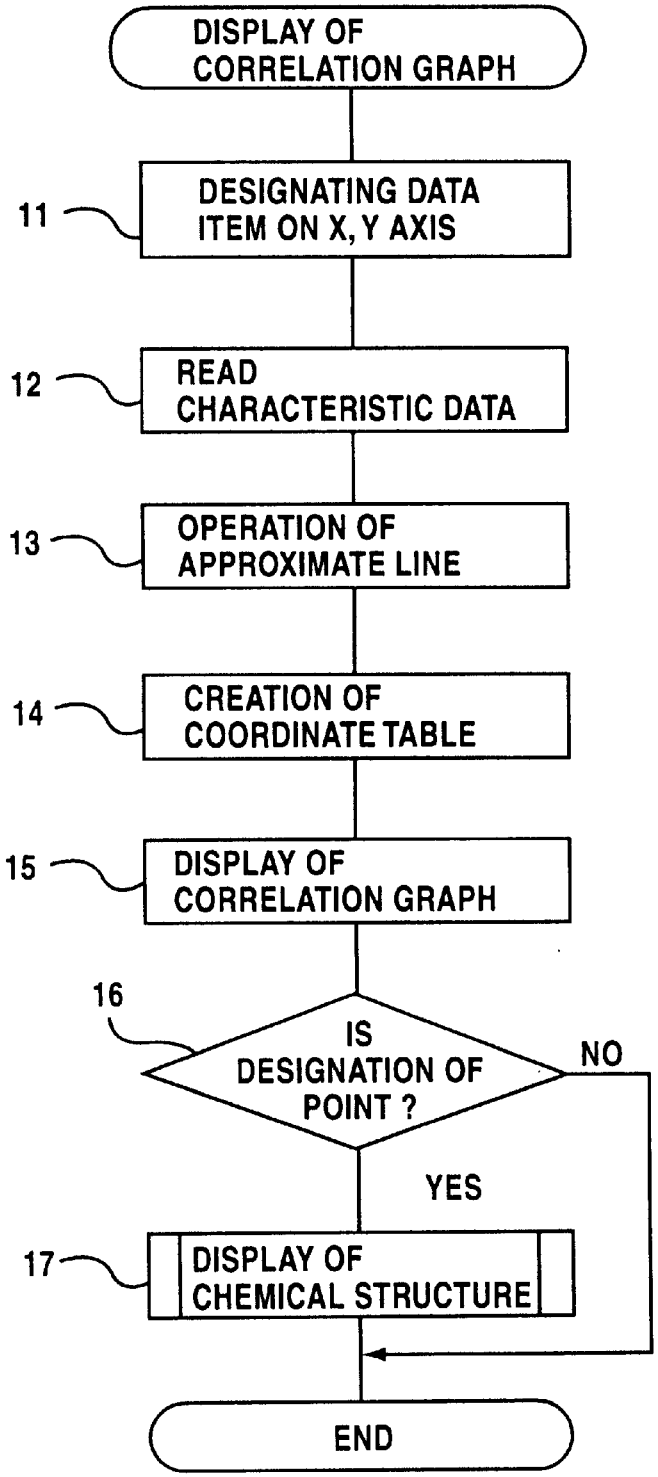
FIG. 13 is a flowchart indicating an outline of the correlation graph display operation.

FIG. 13 is a flowchart indicating the processing operation for displaying the correlation graph.

First, when the correlation graph display mode is designated in the menu screen (not illustrated), since the data item name DH for designating the physical materials on the axes X and Y of the correlation graph CD is displayed as the menu list, the data item name DH (physical material name) of the axes X and Y are respectively designated from the list (step #11). When the data item name DH of the axes X and Y is designated, the respective physical material data DM are read to the work area from the database DB (step #12). Moreover, the compound number ND is also read as well as the physical material data DM.

In order to plot respective compounds on the screen 13a, the coordinates X and Y of the plotting points PP are computed based on the physical material data DM, and a formula for the most approximated straight line AL for plotting points PP is also obtained (step #13). Based on the computed coordinates, a coordinate table TC is generated (step #14). This coordinate table TC stores physical material data of the coordinates X and Y for respectively compound numbers ND.

The correlation graph CD including each plotting point and straight line is displayed on the screen 13a based on the coordinates table TC and a formula of the most approximated straight line (step #15). Of course, an approximated curve can also be displayed as a graph.

Figure 14:
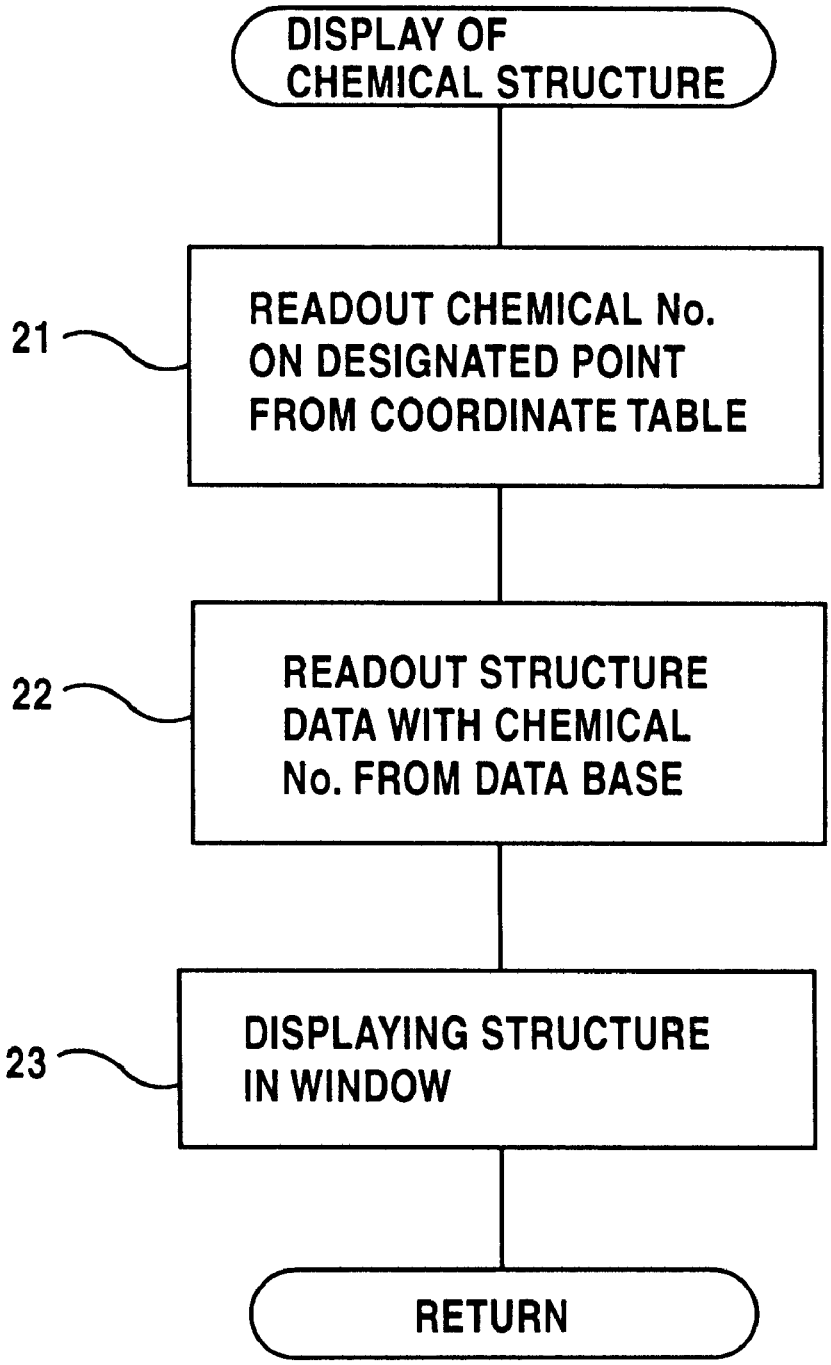
FIG. 14 is a flowchart of the processing for the chemical structure display to the correlation graph.

On the other hand, when the plotting point PP is designated (YES in the step #16), the processing for the chemical structure display is carried out (step #17). FIG. 14 is a flowchart indicating the chemical structure display processing operation. Based on the designated plotting point PP, the compound number ND thereof is read from the coordinate table TC (step #21). A plotting point PP is designated by instructing the data within a circle of a constant radius around the plotting point PP on the screen 13a with a mouse and then clicking such data. The designated plotting point PP is changed to red from black for emphasizing the display.

Next, the chemical structure data DS corresponding to the compound number ND at the designated plotting point read in the step #21 is then read into the work area from the database DB (step #22). Based on the chemical structure data DS, the chemical structure CC is displayed in the window at the lower right position of the plotting point PP (step #23).

According to the third embodiment of the present invention explained above, since a chemical structure CC of a compound corresponding to the plotting point PP is displayed in the window on the screen by designating the plotting point PP in the correlation graph CD, the chemical structure CC can be a key point in the analysis of the investigator, since analyzing the correlation graph CD can be easily visualized on the same screen 13a. It becomes possible for an investigator to study various aspects of the compounds without interrupting his train.

4th Embodiment

The 4th embodiment of the present invention will be explained hereunder. In the chemical data handling system of the present invention, based on the technique for displaying a large data table TD within a limited screen size in the sheet image, various concepts are provided for utilizing table data. The subject matter of the 4th embodiment is a check function for reserving reliability on the occasion of copying part of a data sheet recording experimental data of a certain theme to the compound data sheet for the other theme.

Figure 15:
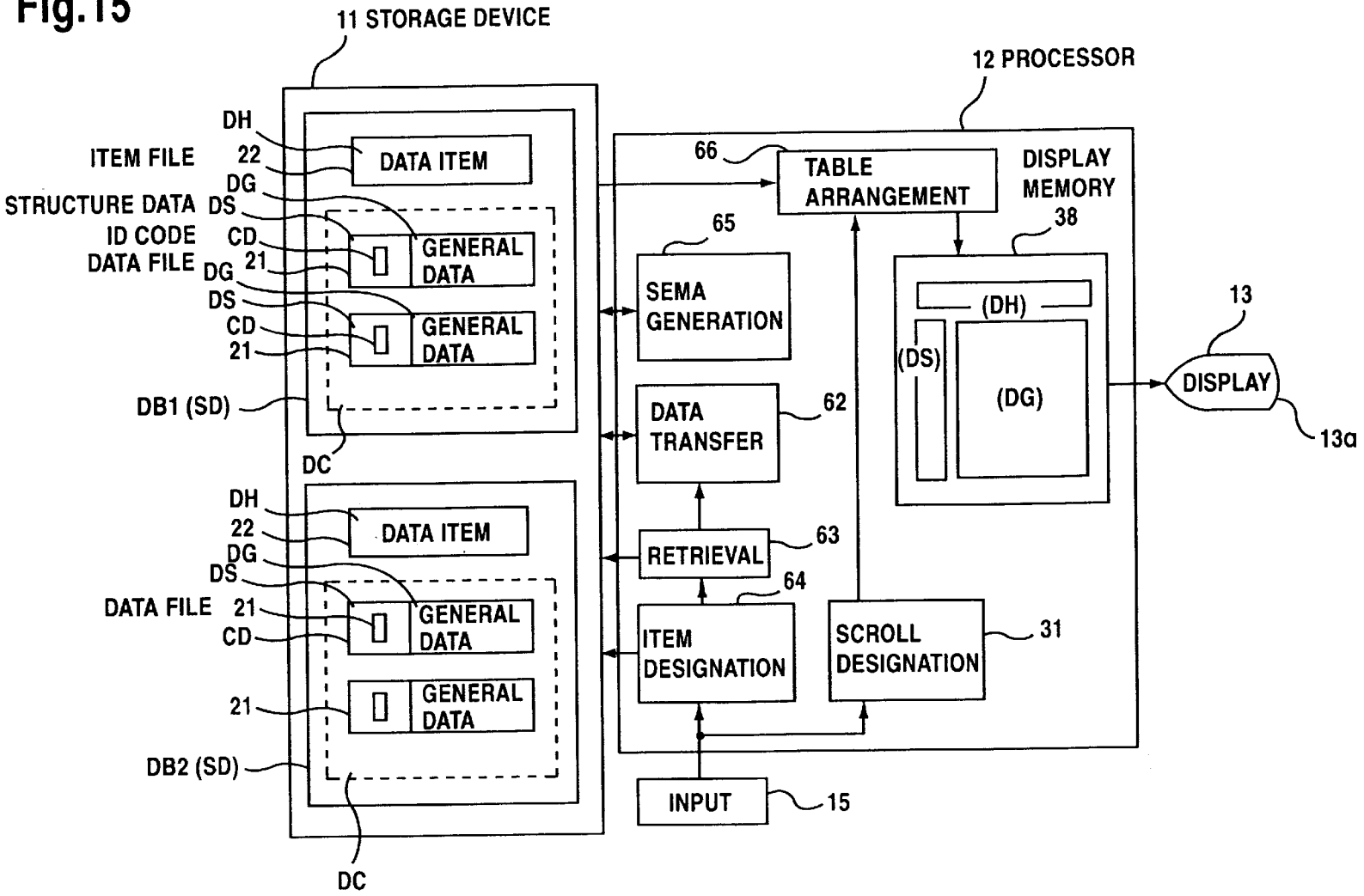
FIG. 15 is a block diagram indicating a functional construction of a chemical data edition and display system in a fourth embodiment.

With reference to FIG. 15 which indicates a system structure providing such a data editing function, a plurality of databases DB1, DB2 consist of a plurality of compound data files 21 and data item name files 22 are stored.

Each compound data file 21 includes a compound data DC consisting of chemical structure data DS and general data DG for compounds like the first embodiment and moreover allows the addition of identification codes CD for uniquely identifying a compound to each compound. The data item name file 22 is a file storing the data item name DH corresponding to compound data DC.

Here, the identification code CD is expressed by a SEMA name which corresponds to a chemical structure on a one to one basis. The SEMA name is regulated for processing chemical structures with a computer and is small in its quantity of data compared to the data (chemical structure data DS explained above) expressing in direct a chemical structure. A SEMA name is generated by a SEMA name generating means 35 when a chemical structure is defined (chemical structure data DS is generated). In this embodiment, a SEMA name is stored as a part of the chemical structure data DS.

Meanwhile, in the case of this system, when a copy mode is selected with a command from the input unit 15, various copyings are possible between data tables or sheets SD1, SD2 corresponding to databases DB1, DB2. For instance, when the one data item name DH of the one sheet is designated and its column is to be copied, all data of a corresponding column in the data sheet DS of the copying side are inserted to the next column position of the designated data item name DH of the data sheet SD in the copied side.

Namely, in this case, general data DG of the designated data item name DH is added to the data sheet SD of the copied side.

In this case, problems do not arise when the number of compounds, the kinds of compounds and arrangements of compounds are equivalent between the compounds included in the data sheet SD in the copying side and the compounds included in the data sheet SD of the copied side. However, if the data are different, erroneous general data DG is copied in the data sheet SD of the copied side. In order to prevent such erroneous copying, whether the compounds are equivalent or different between the sheets of the copying side and copied side by the SEMA name CD, only data of the rows where the SEMA name CD is matched is allowed to be copied.

Therefore, FIG. 15 comprises a data item name designating a means 64 for designating data item name DH to be copied from the data sheet SD in the copying side, a retrieving means 63 for retrieving a compound data file 21 having the SEMA name CD matched with the SEMA name CD in the copying side from the compound data file 21 of data sheet SD of the copied side, a data transfer means 62 for copying general data DG of the designated data item name DH for the compound data file 21 where the SEMA name CD is matched, a scroll designating means 31 for designating contents of a data table TD to be displayed on the screen 13a by designating the horizontal and vertical scrolls, and a data arranging means 66 for reading the compound data DC and data item name DH designated by the scroll designating means 31 from the memory means 11 and then writing such data to the display memory 38 so that the data is arranged as the data table TD on the predetermined area of the screen 13a.

For example, it is here cosidered that the column of "Generic name" of data No. 1 in the data sheet SD1 (table portion TD1) shown in FIG. 3 is designated to copy such data to the next column of data No. 0 of another data sheet SD2 having no data of "Generic Name".

Figure 16:
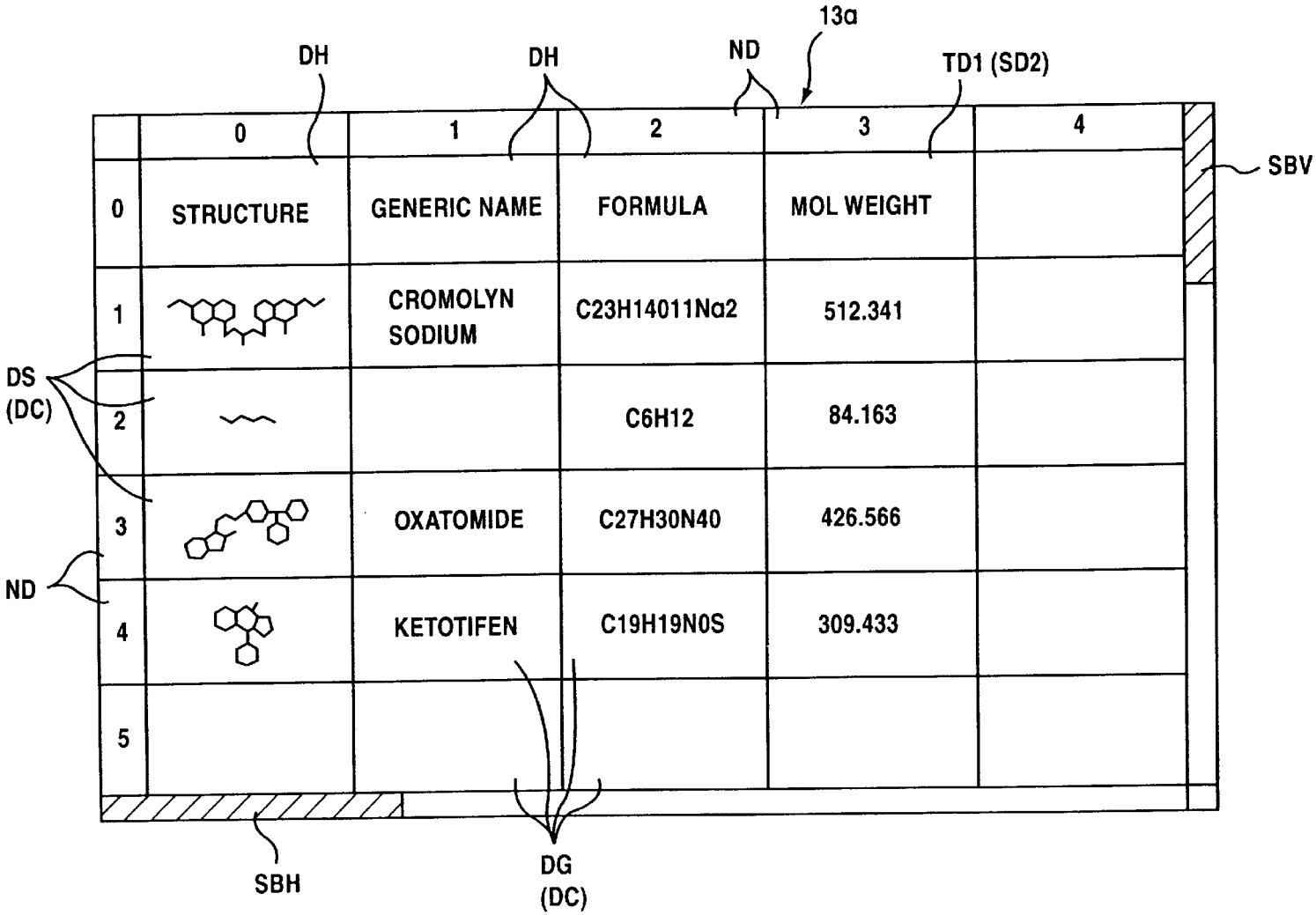
FIG. 16 is a diagram indicating a display example of another data table in which the data column 1 of FIG. 3 is copied.

FIG. 16 indicates the other data sheet SD2 after the copying operation. In the comparison of data DS between sheets (therefore SEMA names CD are compared), the data numbers ND "1", "3", "4" of data sheet SD1 are respectively identical to the data numbers ND "1", "4", "3" of the date sheet SD2 and there is no chemical structure data DS, in the data sheet SD1, corresponding to the data numbers ND "2" and "5" of the data sheet SD1.

Accordingly, in the data sheet SD2, the general data DG "Cromolyn sodium", "Oxatomide", "Ketotifen" sent from the data table TD1 are written to the position corresponding to the chemical structure data DS having the data numbers ND "1", "3", "4" and nothing is written as a blank to the position corresponding to the chemical structure data DS having the data numbers ND "2" and "5".

As explained above, when the copying is carried out after designating the data item name DH in the data sheet SD1 in the copying side, the chemical structure data DS of data sheet SD1 in the copying side are all checked, by comparison with SEMA name CD, whether there is the same chemical structure data DS or not in the data sheet SD2 of copied side. The general data DG is written for the matched data sheets but such general data DG are rejected for the data sheets having no matched SEMA name CD.

Figure 17:
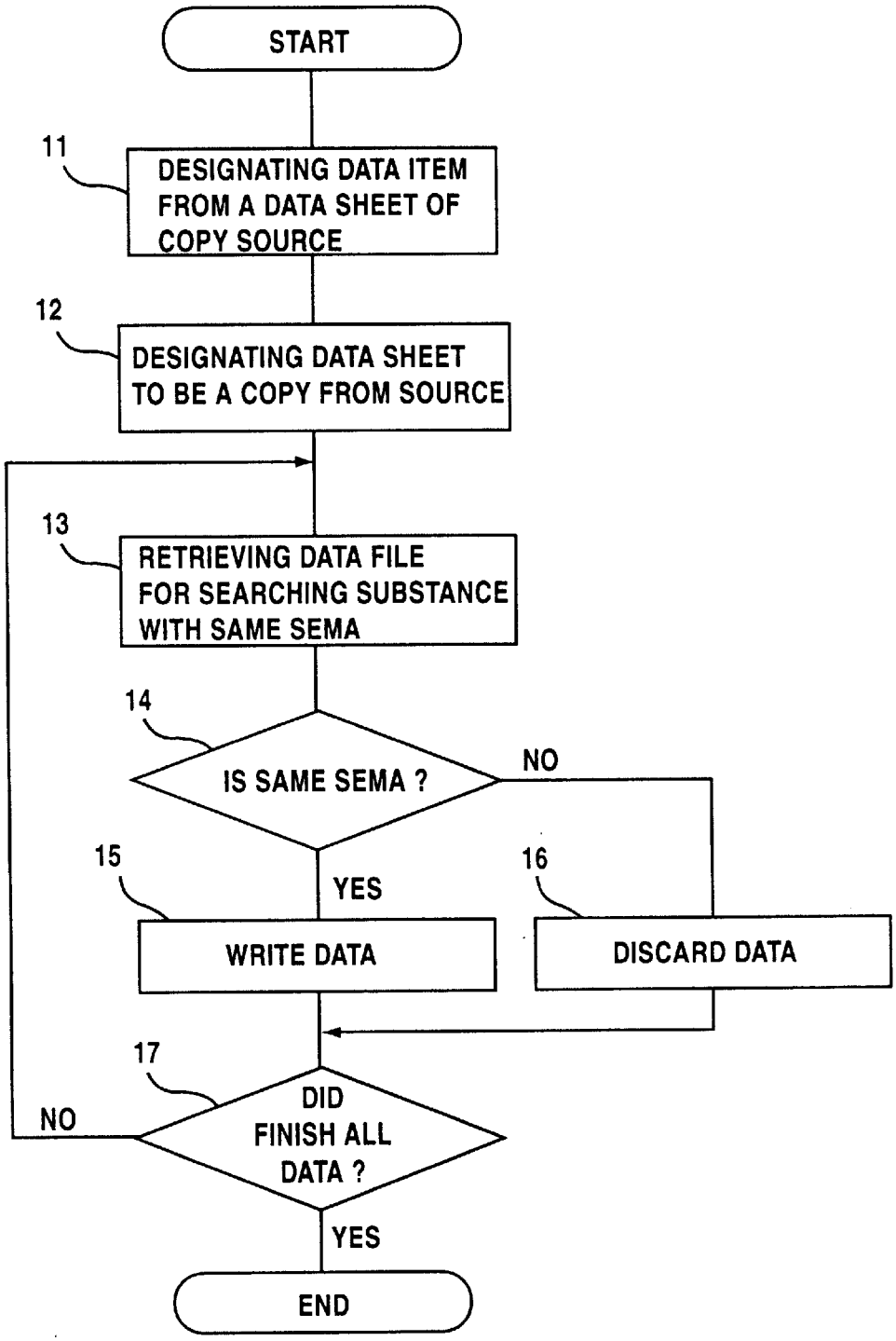
FIG. 17 is a flowchart for executing partial copying of data table.

FIG. 17 is a flowchart of the copy check operation explained above.

(1) First, the data item name DH to be copied from the data sheet SD1 in the copying side is designated (step #11).

(2) A data sheet SD2 of the copied side is designated (step #2).

(3) For the data sheet SD1 of the copying side, the compound data file 21 in the copied side having the same SEMA name CD as that in the copying side is retrieved in the sequence of the data number ND of the chemical structure data DS (step #13).

(4) It is checked whether there is the same SEMA name CD or not (step #14).

(5) When in case there is the same SEMA namde CD, such data is written into the compound data file 21 (step #15).

(6) In case there is no same SEMA name CD, such data is rejected (step #16).

(7) Checking is continued for all chemical structure data DS in the copying side (step #17).

According to the embodiment explained above, when copying is carried out by designating the data item name DH at the time of copying the compound data DC between the data sheets SD, it can be prevented that data is correctly written into the compound data file 21 of the same compound and error data is copied for a different compound, even between the data sheets SD where the kinds of compound, the quantity of the compound the arrangement of the compound (chemical structure data DS) are different.

5th Embodiment

The 5th embodiment of the present invention is intended to add the special expressions which are used in this field for the chemical structure data as the key information of the chemical data table explained in the preceding embodiment. Namely, in the field of chemistry, special expressions such as "Mercush expression", "same meaning expression", "repeat expression" and "partial structure designation expression"are added as well as the bond line for indicating atomic symbols and coupling relation thereof for expressing chemical structures. In order to input and express special expressions associated with such chemical structure to a computer and then display such special expressions, individual chemical structure information areas CS stored in the chemical structure data files DS in the storage device are formed in the format shown in FIG. 18.

Figure 18:
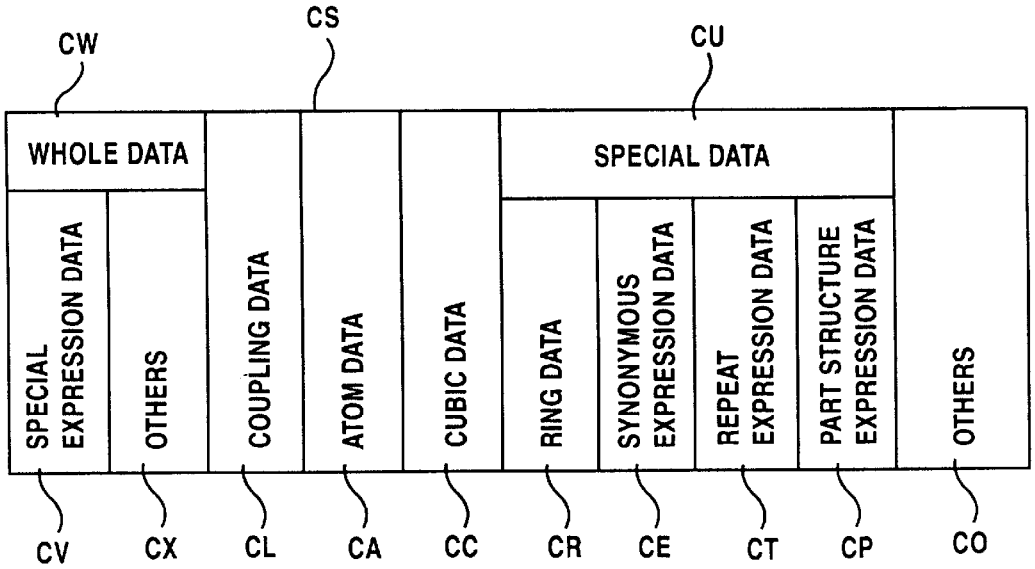
FIG. 18 is a diagram indicating a data format in a chemical structure information area.

With reference to FIG. 18, the chemical structure information area CS includes total information CW, atomic information CA, coupling information CL, cubic information CC, special information CU and other information CO.

The total information CW includes special expression information CV and the other information CX.

Special information CU is capable of including ring information CR, same meaning expression information CE, repeat expression information CT, and partial structure designation expression information CP.

The special expression information CV indicates a number of special expressions NS included in chemical structure (namely, a number of information included as the special information CU) and a total number NR of R substructures.

The other information CX indicates a total number of atoms NA and a number of couplings NL.

The coupling information CL indicates the coupling relation of atoms AT, including the position number NP of atoms AT being coupled and its type of coupling TL, namely, for example, ring, single coupling and double coupling, etc.

The atomic information CA indicates the position number NP of atom AT, atomic symbol MA indicating a type of atom AT, coordinates TC of atom AT in the chemical structure, the number of special expressions NE related with atom AT and the number of special expressions added to the special information CU.

The ring information CR indicates the atoms which form a ring included in a chemical structure. The ring information CR includes data which shows whether a ring is an aromatic ring or not, the number of atoms AT forming a ring and the position number NP of atoms AT forming a ring. With this ring information CR, the coupling relation between atoms AT forming a ring and a group coupled therewith is replaced with a coupling relation between the ring and group. The chemical structure of the inductive material due to differences in position of a group can be expressed with data, enabling a Mercush expression EM which indicates that a group is attached to an undefined position of a ring.

Figure 19:
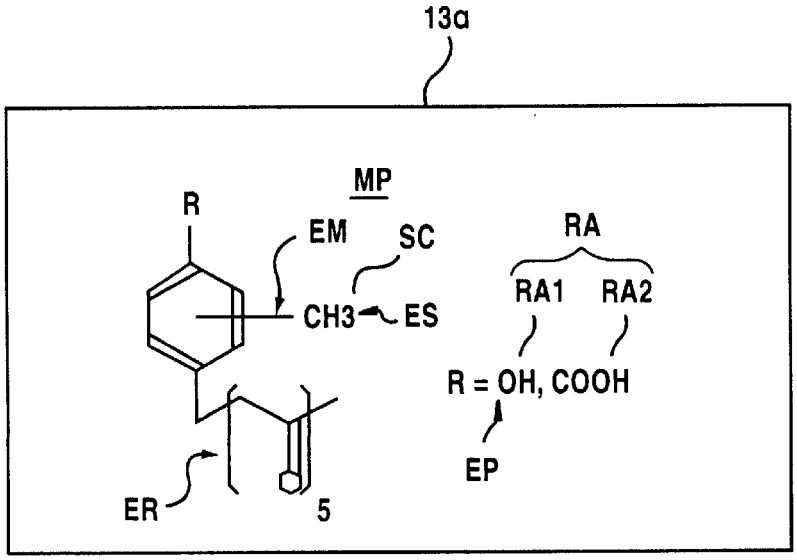
FIG. 19 is a diagram indicating a display example of chemical structural formulas including special expressions.

Namely, in the case of a Mercush expression EM shown in FIG. 19, it is expressed that a methyl group "CH3" may be attached to anywhere in the benzen ring, but since it can be recognized by the ring information CR that with which carbon atoms a benzene ring is formed, the entirety of the benzene ring can be processed as if it were formed by only one atom, in the coupling relation between the methyl group "CH3" and the benzene ring.

Next, the same meaning expression information CE indicates atoms AT forming a substituent of a partial chemical structure, for example, the substituent and a string of characters SC for indicating such a substituent. In other words, such same meaning expression information CE indicates atoms AT forming a substituent corresponding to a string of characters SC expressed in the structural formulas. This information CE includes information such as a string of characters SC indicated, the number of atoms AT forming a substituent and the position number NP of atoms AT forming a substituent. Therefore, a particular chemical structure such as a substituent can be expressed by a string of characters SC in place of atoms and the same meaning expression ES is enabled for expressing that a string of characters SC is identical to a particular chemical structure.

Specifically, in the same meaning expression ES shown in FIG. 19, it is indicated that a string of characters "CH3" is processed in the same meaning as the chemical structure of methyl group "CH3" but the same meaning expression information CE indicates that a string of characters "CH3" corresponds to a chemical structure of the methyl group "CH3".

Next, the repeat expression information CT indicates atoms AT forming a basic structure and the number of times of repetition of the basic structure in case a partial chemical structure included in the chemical structure is formed by several times of repetition of a particular basic structure. In other words, this information indicates, in regard to the repeat expression ER indicated in the structural formula, the number of times of repetition and of atoms AT forming a chemical structure corresponding to such a repeat expression ER. The repeat expression ER includes information such as the maximum and minimum values of repetition, the number of atoms AT forming a chemical structure corresponding to the repeat expression ER and the position number NP of atoms. Thus, in case the basic structure is repeated several times, the chemical structure can be expressed only by the basic structure and the repeat expression ER can be enabled to express n times of repetition of the structure (basic structure) enclosed by the parentheses.

Namely, the repeat expression ER shown in FIG. 19 indicates that the basic structure enclosed by the parenthesis are repeated five times, but the repeat expression information CT indicates that the basic structure corresponds to an actual chemical structure based on such a basic structure.

Next, the partial structure designation expression information CP indicates information about the other atom information CA and coupling information CL of an atom expressing a chemical structure of a group included in the chemical structure. In other words, this information indicates, in regard to the group "R" indicated in the structural formula, a chemical structure (R substructure) of the one or several kinds of substituents to be substituted in place of the group "R". The partial structure designation expression information CP includes infomation such as position number NP of group "R", the number of R substructures and the chemical structure information CS number indicating the chemical structure of R substructure. Thereby, the one or several groups included in a chemical structure can be expressed with particular symbols (for example, "R"). The partial structure designation expression EP, in which the one or several kinds of groups indicated by a string of characters can selectively attach to the position indicated by "R" in the structural formula, can be realized.

That is, the partial structure designation expression EP shown in FIG. 19 indicates that a functional group "OH" or "COOH" is selectively attached to the position indicated by "R" but the partial structure designation expression information CP indicates correspondence to the other chemical structure information area CS (chemical structure information area CS1) indicating a chemical structure corresponding to the functional groups "OH" and "COOH".

Next, a process of generating a chemical structure information area CS by drawing of chemical structure will be explained with reference to the flowchart of FIG. 20.

Figure 20B:
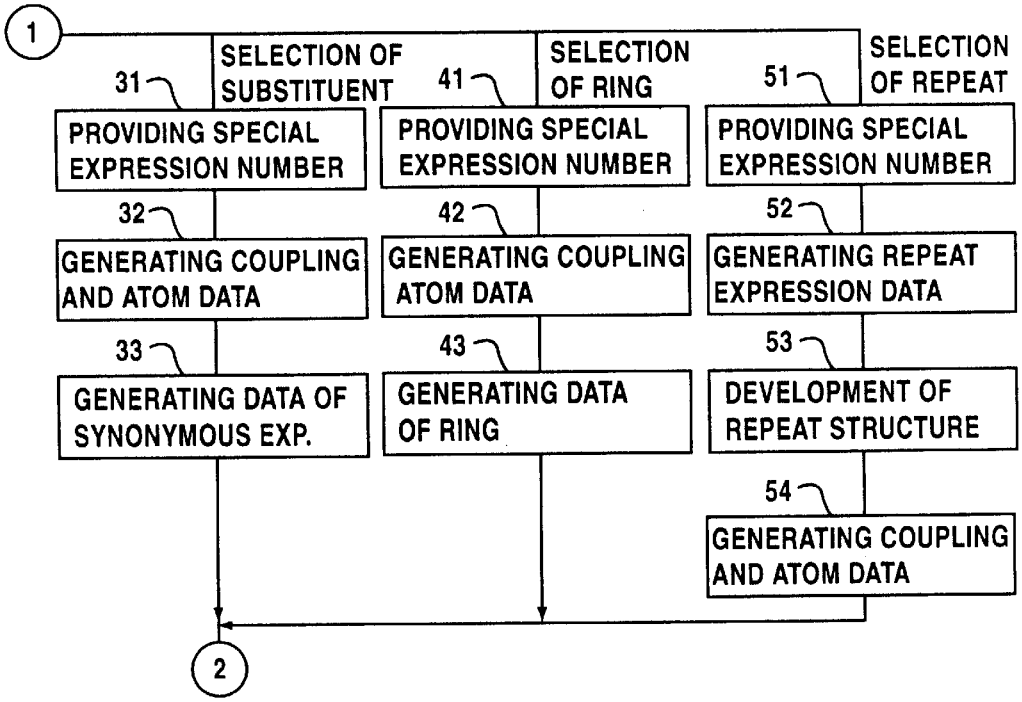
FIGS. 20(a) and (b) are flowcharts indicating structure data generating process at the time of drawing chemical structures.
Figure 20A:
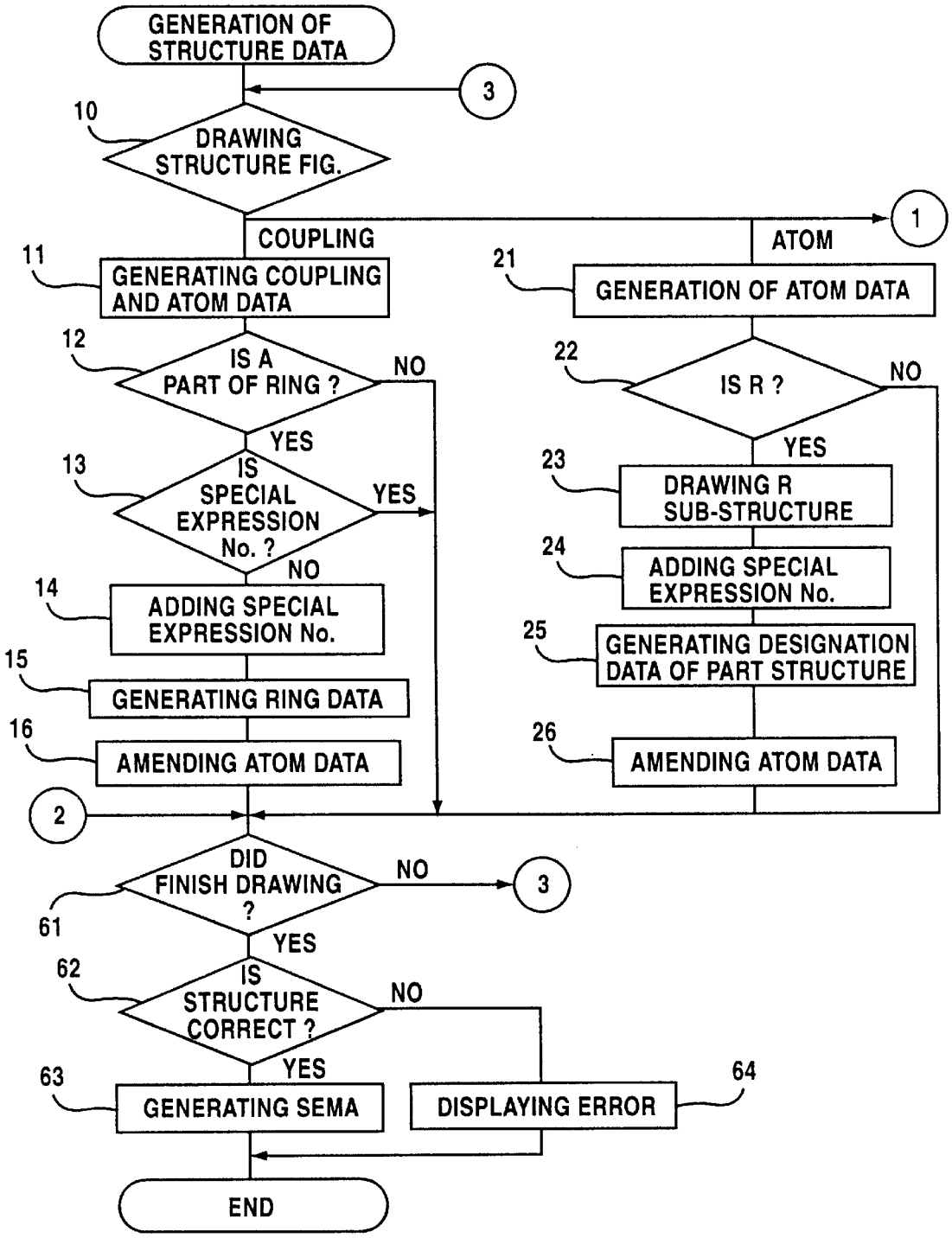

FIG. 20 is a flowchart indicating the chemical structure information generation processing during the drawing of a chemical structure.

First, in the step #10, a part or a function required for the part to be drawn, for example, an atom, a coupling, a ring and a repeat are selected from the drawing menu on the screen 13a. In accordance with the selected contents, the processing branches to any of the steps #11, 21, 31, 41, 51.

When coupling is selected, coupling information CL and atom information CA are generated (step #11) for the bond line and atoms AT at both ends thereof are displayed on the screen 13a.

If a ring is formed by the bond line (YES in the step #12), the special expression number NU is given (step #14) when the special expression number NU is not yet given. Then, ring information CR is generated (step #15) and the atom information CA in relation thereto is corrected (step #16).

When an atom is selected in the step #10, atom information CA is generated for atoms AT arranged on the screen 13a (step #21).

When the arranged atom AT is "R" (YES in the step #22), it means that the partial structure designation expression EP is selected and the screen is changed to draw the R substructure which is the chemical structure corresponding to "R" (step #23). On the changed screen the processings similar to the flowchart are carried out. Accordingly, an operator draws the R substructure in the same manner as explained above. With the drawing of the R substructure, a chemical structure information area CS different from that being generated currently is generated.

Upon completion of the drawing of the R substructure, the special expression number NU is given (step #24), the partial structure designation expression information CP is generated (step #25) and the atom information CA relation to such information is corrected (step #26).

When a substituent is selected in the step #10, it means that the same meaning expression ES is selected, the special expression number NU is given (step #31) and the coupling information CL, atom information CA and same meaning expression information CE are generated (steps #32, 33).

When a ring is selected in the step #10, it is probable that the Mercush expression EM may be conducted. The special expression number NU is given (step #41), and coupling information CL, atom information CA and ring information CR are generated (steps #42, 43).

When a repeat is selected in the step #10, it means that the repeat expression ER is selected. The special expression number NU is given (step #51), the repeat expression information CT is generated (step #52) and the coupling information CL and atom information CA are generated by development of a repeat structure based on generation of repeat expression information (steps #53, 54).

These processings are conducted until the end of the drawing (step #61). When drawing is completed, it is checked whether the chemical structure is correct or not (step #62). When it is correct, a SEMA name is generated by computation (step #63). If it is incorrect, an error display is carried out (step #64).

As explained above, the present invention provides a system which usefully supports investigation work through the display of chemical structures including special expressions which are used by investigators.

What we claim are:

1. A chemical data handling system for editing and displaying compound data table consisting of chemical structure data and general data for a plurality of compounds on a display screen, comprising:

means for arranging chemical structure data and general data of at least one compound in the direction of axis X of the display screen;

means for arranging a plurality of chemical data for different compounds in the direction of axis Y crossing the direction of axis X of the display screen;

means for arranging data item names corresponding to said chemical structure and general data of said at least one compound in the direction of axis X at a side of the display screen; and means for scrolling a compound data table formed from said chemical, chemical structure and general data in the directions of said axis X and axis Y, wherein said scroll means fixes data of a column displaying structures of compounds and shifts remaining general data columns in the direction of said axis X at the time of scrolling in the direction of said axis X.

2. A chemical data handling system claimed in claim 1, wherein said scroll means fixes data of a row of data item names arranged in the side of the display screen and shifts data of rows of remaining compounds in the direction of said axis Y at the time of scrolling the formed compound data table in the direction of said axis Y.

3. A chemical data handling system claimed in claim 1, wherein said scroll means fixes data of a row of data item names in an uppermost line of the display screen along said axis X and shifts data of rows of remaining compounds in the direction of said axis Y at the time of scrolling the formed compound data table in the direction of said axis Y.

4. A compound data display unit comprising:

a plurality of compound data files storing compound data (DC) consisting of chemical structure data (DS) and general data (DG) for each of a plurality of compounds;

a data item name file storing data item names (DH) corresponding to said compound data for said plurality of compounds;

display means having a screen for displaying said compound data (DC) and said data item names (DH);

scroll instruction means for instructing scrolling in a direction of an axis X or an axis Y on said screen;

data item name readout means for reading data item names (DH) corresponding to said chemical structure data (DS) and data item names (DH) at a position in the direction of said axis X instructed by said scroll instruction means from said data item name file;

chemical structure data readout means for reading chemical structure data (DS) at a position in the direction of said axis Y instructed by said scroll instruction means from said compound data file;

general data readout means for reading general data (DG) at a position instructed by said scroll instruction means;

data item name arranging means for arranging obtained data item names (DH) in the direction of said axis X on said screen;

chemical structure data arranging means for arranging obtained chemical structure data (DS) at positions corresponding to respective data item names (DH) in the direction of said axis Y orthogonally crossing said direction of said axis X on said screen; and general data arranging means for arranging obtained general data (DG) at positions on said screen corresponding to respective data item names (DH) and respective chemical structure data (DS).

5. A chemical data handling system for displaying compound data (DC) consisting of chemical structure data (DS) and general data (DG) of a plurality of compounds on the screen, comprising:

a compound data table display mode for displaying said compound data (DC) in the form of a table on said screen by arranging chemical structure data (DS) of each compound in a direction of axis Y and general data (DG) of each chemical structure data (DS) in a direction of axis X orthogonally crossing the direction of said axis Y; and a structure table display mode for arranging chemical structure data (DS) of each compound in the form of a matrix in the directions of said axes X and Y to display such data on said screen, wherein said display modes can be switched by input means and displayed on the screen.

6. A chemical data handling system claimed in claim 5, wherein designated general data (DG) is additionally displayed in the vicinity of each chemical structure data (DS) displayed on said screen in said structure table display mode.

7. A compound data display unit comprising:

a plurality of compound data files storing compound data (DC) consisting of chemical structure data (DS) and general data (DG) for each of a plurality of compounds;

a data item name file for storing data item names (DH) corresponding to said compound data (DC);

display means having a screen for displaying said compound data (DC) and said data item names (DH);

compound data table arranging means for displaying said compound data (DC), in a table format, on said screen by arranging chemical structure data (DS) of each of said plurality of compounds in a direction of axis Y and arranging general data (DG) of each chemical structure data (DS) in a direction of axis X orthogonally crossing the direction of said axis Y;

structure table arranging means for displaying chemical structure data (DS) of each of said plurality of compounds on said screen by arranging such data in the form of a matrix in the directions of said axes X and Y; and switching means for switching an arrangement by said compound data table arranging means and said structure table arranging means.

8. A chemical data handling system formed to display a correlation graph (CD), on the screen, in regard to two kinds of physical material data (DM) in a database (DB) storing compound data (DC) including chemical structure data (DS) of each of a plurality of compounds and a plurality of physical material data (DM) for each of said plurality of compounds, wherein a chemical structure (CC) corresponding to a relevant plotting point (PP) is displayed on said screen by designating the plotting point (PP) of the correlation graph (CD) displayed on said screen.

9. A chemical data handling system claimed in claim 8, wherein said chemical structure (CC) is window-displayed on the same screen together with the correlation graph (CD).

10. A chemical data handling system, comprising:

a compound data file for storing compound data (DC) consisting of chemical structure data (DS) and general data (DG) for each of a plurality of compounds;

first and second databases each consisting of a plurality of compound data files; and data transfer means for transferring said compound data (DC) to the second database in a transferred side from the first database in a transferring side, wherein an identification code (CD) which is capable of uniquely identifying each of said plurality of compounds is stored in said compound data file, and relevant compound data (DC) is transferred only when an identification code (CD) of a compound data file in the transferring side matches with an identification code (CD) of a compound data file in the transferred side.

11. A chemical structure handling system for expressing a chemical structure with data depending on atom information (CA) indicating a kind and a position of an atom (AT), comprising:

a compound data file storing, for each of a plurality of compounds, compound data (DC) consisting of chemical structure data (DS), general data (DG), coupling information (CL) for indicating a coupling condition between atoms (AT) and special information (CU) in relation to a partial chemical structure included in the chemical structure of each of the plurality of compounds;

processing means for processing chemical structures to be displayed based on the atom information, said coupling information and said special information;

display means having a screen for displaying the chemical structures; and drawing means for drawing the chemical structures processed by said processing means on the screen of said display means.

*12. A chemical data handling system for displaying a compound data table including chemical structure data and general data for a plurality of compounds on a display screen, comprising:*

*means for arranging chemical structure data and general data of at least one compound in the direction of axis X of the display screen;*

*means for arranging a plurality of compound data for different compounds in the direction of axis Y crossing the direction of axis X of the display screen;*

*means for arranging data item names corresponding to said chemical structure and general data of said at least one compound in the direction of axis X at a side of the display screen; and*

*means for scrolling a compound data table formed from said chemical structure data and general data in the directions of said axis X and axis Y, wherein said scroll means fixes data of at least one column displaying structures of compounds and shifts remaining general data columns in the direction of said axis Y at the time of scrolling in the direction of said axis X.*

*13. A chemical data handling system as claimed in claim 12, wherein said scroll means fixes data of a row of data item names arranged in the side of the display screen and shifts data of rows of remaining compounds in the direction of said axis Y at the time of scrolling the formed compound data table in the direction of said axis Y.*

*14. A chemical data handling system formed to display a correlation graph (CD), on a screen, in regard to at least one kind of material data (DM) in a database (DB) storing compound data (DC) including chemical structure data (DS) of each of a plurality of compounds and material data (DM) for each of said compounds, comprising:*

*means for designating a plotting point (PP) of the correlation graph (CD) displayed on said screen; and*

*means for displaying a chemical structure (CC) corresponding to the relevant plotting point (PP) on said screen.*

*15. A chemical data handling system formed to display a correlation graph (CD), on a screen, in regard to at least one kind of material character data (DM) in a database (DB) storing compound data (DC) including chemical structure data (DS) of each of a plurality of compounds and material character data (DM) for each of said compounds, comprising:*

*means for displaying a plotting point (PP) for a compound on said screen;*

*means for designating a plotting point (PP) of the correlation graph (CD) displayed on said screen; and*

*means for displaying a chemical structure (CC) corresponding to the relevant plotting point (PP) on said screen.*

*16. A chemical data handling system as claimed in claim 14 or 15, further comprising:*

*means for making a visibly distinguishable effect on the designated plotting point (PP) on the screen.*

*17. A chemical data handling system as claimed in claim 14 or 15, further comprising:*

*means for changing color of the designated plotting point (PP) on the screen.*

*18. A computer readable memory having a computer program thereon for directing a computer to control the operation of a display for displaying a data table including chemical structure data and general data for a plurality of compounds, said computer program comprising the steps for controlling the computer to:*

*arrange chemical structure data and general data of at least one compound for display in the direction of axis X on a display screen;*

*arrange a plurality of general data for different compounds for display in the direction of axis Y crossing the direction of axis X on the display screen;*

*arrange data item names corresponding to the chemical structure and general data of the at least one compound for display in the direction of axis X on a side of the display screen; and*

*scroll a compound data table formed from the chemical structure data and general data in the directions of the axis X and axis Y, such that the data of at least one column displaying structures of compounds is fixed and the remaining general data columns are shifted in the direction of the axis Y at the time of scrolling in the direction of the axis X.*

*19. A computer program controlled process for controlling the operation of a display for displaying a data table including chemical structure data and general data for a plurality of compounds, said process comprising the steps of:*

*arranging chemical structure data and general data of at least one compound for display in the direction of axis X on a display screen;*

*arranging a plurality of general data for different compounds for display in the direction of axis Y crossing the direction of axis X on the display screen;*

*arranging data item names corresponding to the chemical structure data and general data in the directions of the axis X on a side of the display screen; and*

*scrolling a compound data table formed from the chemical structure data and general data in the directions of the axis X and axis Y, such that the data of at least one column displaying structures of compounds is fixed and the remaining general data columns are shifted in the direction of the axis Y at the time of scrolling in the direction of axis X.*

*20. A computer readable memory having a computer program thereon for directing a computer to control the operation of a display for displaying a correlation graph in regard to at least two kinds of material data in a database storing compound data including chemical structure data of each of a plurality of compounds and a plurality of material*

*data for each of said compounds, said computer program comprising the steps for controlling the computer to:*

*designate a plotting point of the correlation graph on the display screen; and*

*display a chemical structure corresponding to the relevant plotting point on the display screen.*

*21. A computer program controlled process for controlling the operation of a display for displaying a data table including chemical structure data and general data for a plurality of compounds, for displaying a correlation graph in regard to at least two kinds of material data in a database storing compound data including chemical structure data of each of a plurality of compounds and a plurality of material data for each of said compounds, said process comprising the steps of:*

*designating a plotting point of the correlation graph on the display; and*

*displaying a chemical structure corresponding to the relevant plotting point on the display.*

* * * * *